(12) United States Patent
Lim et al.

(10) Patent No.: US 12,119,462 B2
(45) Date of Patent: Oct. 15, 2024

(54) SENSING DEVICE FOR DETECTING ANALYTES IN BATTERIES

(71) Applicant: Lyten, Inc., San Jose, CA (US)

(72) Inventors: Sung H. Lim, Mountain View (CA); Karel Vanheusden, Woodside, CA (US); Daniel Cook, Woodside, CA (US); George Clayton Gibbs, Santa Clara, CA (US)

(73) Assignee: Lyten, Inc., San Jose, CA (US)

( * ) Notice: Subject to any disclaimer, the term of this patent is extended or adjusted under 35 U.S.C. 154(b) by 722 days.

(21) Appl. No.: 17/182,082

(22) Filed: Feb. 22, 2021

(65) Prior Publication Data

US 2021/0172905 A1 Jun. 10, 2021

Related U.S. Application Data

(63) Continuation-in-part of application No. 16/887,293, filed on May 29, 2020, now Pat. No. 11,137,368,
(Continued)

(51) Int. Cl.
*H01M 10/48* (2006.01)
*B01J 20/28* (2006.01)
(Continued)

(52) U.S. Cl.
CPC ....... *H01M 10/48* (2013.01); *B01J 20/28066* (2013.01); *C01B 32/182* (2017.08);
(Continued)

(58) Field of Classification Search
CPC . H01M 10/4228; H01M 10/48; C01B 32/182; G01N 29/036; G01N 2291/0255;
(Continued)

(56) References Cited

U.S. PATENT DOCUMENTS

| 5,520,789 A | 5/1996 | Takahashi et al. |
| 5,725,754 A | 3/1998 | Belford |

(Continued)

FOREIGN PATENT DOCUMENTS

| CN | 101682009 A | * | 3/2010 | ............. H01G 11/82 |
| CN | 102754272 A | * | 10/2012 | ........... B60L 11/1809 |

(Continued)

OTHER PUBLICATIONS

Ma et al. ("Printed Spiral Multi-Coil Based Inductive-Power-Link for Wireless Sensor Applications"; Department of Electrical and Computer Engineering, The University of Alabama at Birmingham, Birmingham, AL; 2016; pp. 1-7).*

(Continued)

*Primary Examiner* — Eric D Lee
(74) *Attorney, Agent, or Firm* — Paradice & Li LLP

(57) ABSTRACT

A sensing device configured to monitor a battery pack is disclosed. The sensing device may include a plurality of carbon-based sensors enclosed within the battery pack. Each sensor coupled may be between a corresponding pair of electrodes, and may include a plurality of 3D graphene-based sensing materials. In some instances, the 3D graphene-based sensing materials of a first sensor may be functionalized with a first material configured to detect a presence of each analyte of a first group of analytes, and the 3D graphene-based sensing materials of a second sensor may be functionalized with a second material configured to detect a presence of each analyte of a second group of analytes.

25 Claims, 28 Drawing Sheets

Related U.S. Application Data which is a continuation-in-part of application No. 16/706,542, filed on Dec. 6, 2019, now Pat. No. 10,955,378, which is a continuation of application No. 16/239,423, filed on Jan. 3, 2019, now Pat. No. 10,502,705.

(60) Provisional application No. 62/815,927, filed on Mar. 8, 2019, provisional application No. 62/613,716, filed on Jan. 4, 2018, provisional application No. 62/979,095, filed on Feb. 20, 2020, provisional application No. 63/088,541, filed on Oct. 7, 2020.

(51) Int. Cl.
  *C01B 32/182* (2017.01)
  *G01N 29/036* (2006.01)
  *H01M 10/42* (2006.01)
  *G01N 27/12* (2006.01)

(52) U.S. Cl.
  CPC ...... *G01N 29/036* (2013.01); *H01M 10/4228* (2013.01); *C01B 2204/04* (2013.01); *C01B 2204/22* (2013.01); *C01B 2204/32* (2013.01); *G01N 27/127* (2013.01)

(58) Field of Classification Search
  CPC ......... G01N 2291/0256; G01N 27/127; G01N 27/4145; G01N 27/4146; B01J 20/205
  See application file for complete search history.

(56) References Cited

U.S. PATENT DOCUMENTS

| | | | |
|---|---|---|---|
| 6,359,444 B1 | 3/2002 | Grimes | |
| 6,997,039 B2 | 2/2006 | Rao et al. | |
| 8,281,642 B2 | 10/2012 | Lee et al. | |
| 8,364,419 B2* | 1/2013 | Potyrailo | G01N 27/026 702/24 |
| 8,567,232 B2 | 10/2013 | Ackley et al. | |
| 8,736,425 B2 | 5/2014 | Potyrailo | |
| 8,754,454 B2 | 6/2014 | Bryant et al. | |
| 8,877,370 B2 | 11/2014 | Kim | |
| 9,038,443 B1 | 5/2015 | Pace et al. | |
| 9,063,079 B2 | 6/2015 | Eckhardt et al. | |
| 9,088,054 B2 | 7/2015 | Lukso et al. | |
| 9,267,993 B2 | 2/2016 | Farmer et al. | |
| 9,304,102 B2 | 4/2016 | Day et al. | |
| 9,395,343 B2 | 7/2016 | Schmid et al. | |
| 9,612,690 B2 | 4/2017 | Zirkl et al. | |
| 9,678,036 B2 | 6/2017 | Balandin | |
| 9,735,279 B2 | 8/2017 | Sato et al. | |
| 9,869,651 B2 | 1/2018 | Akinwande et al. | |
| 9,927,390 B2 | 3/2018 | Satou | |
| 10,031,097 B1 | 7/2018 | Han et al. | |
| 10,502,705 B2 | 12/2019 | Stowell et al. | |
| 10,502,793 B2* | 12/2019 | Hsieh | G01R 31/392 |
| 10,989,684 B2* | 4/2021 | Grabbert | G01N 27/308 |
| 11,200,474 B2* | 12/2021 | Swager | G01N 33/0075 |
| 11,555,799 B2* | 1/2023 | Lanning | H01M 4/667 |
| 11,688,895 B1* | 6/2023 | Gibbs | H01M 10/488 429/90 |
| 2001/0020383 A1 | 9/2001 | Moos et al. | |
| 2004/0204915 A1 | 10/2004 | Steinthal et al. | |
| 2007/0048181 A1 | 3/2007 | Chang et al. | |
| 2007/0056352 A1 | 3/2007 | Birkhofer et al. | |
| 2008/0047329 A1* | 2/2008 | Breed | G01N 35/00871 73/61.41 |
| 2008/0135614 A1 | 6/2008 | Werner et al. | |
| 2009/0145233 A1 | 6/2009 | Eklund et al. | |
| 2010/0268479 A1* | 10/2010 | Potyrailo | G01N 27/026 702/23 |
| 2012/0006102 A1 | 1/2012 | Bryant et al. | |
| 2012/0116683 A1* | 5/2012 | Potyrailo | G01N 27/026 977/773 |
| 2012/0235690 A1* | 9/2012 | Potyrailo | G01N 27/028 324/652 |
| 2013/0040397 A1 | 2/2013 | Star et al. | |
| 2014/0011286 A1 | 1/2014 | Potyrailo et al. | |
| 2014/0305191 A1 | 10/2014 | Schmid et al. | |
| 2014/0336952 A1 | 11/2014 | Kellaway et al. | |
| 2015/0008486 A1 | 1/2015 | Bryant et al. | |
| 2015/0246814 A1* | 9/2015 | Li | C08L 71/02 428/408 |
| 2015/0377824 A1 | 12/2015 | Ruhl et al. | |
| 2016/0091447 A1 | 3/2016 | Yu et al. | |
| 2016/0123947 A1 | 5/2016 | Briman et al. | |
| 2016/0169824 A1 | 6/2016 | Shin et al. | |
| 2016/0177387 A1 | 6/2016 | Roy et al. | |
| 2016/0195488 A1 | 7/2016 | Ensor et al. | |
| 2016/0282312 A1 | 9/2016 | Cable et al. | |
| 2016/0290956 A1 | 10/2016 | Sato et al. | |
| 2017/0181669 A1 | 6/2017 | Lin et al. | |
| 2017/0276634 A1 | 9/2017 | Saffell et al. | |
| 2017/0330004 A1 | 11/2017 | Gibson | |
| 2017/0350882 A1 | 12/2017 | Lin et al. | |
| 2017/0356869 A1 | 12/2017 | Koenig et al. | |
| 2018/0059080 A1 | 3/2018 | Jun et al. | |
| 2018/0136157 A1 | 5/2018 | Harada et al. | |
| 2018/0285711 A1 | 10/2018 | Swager et al. | |
| 2019/0064143 A1 | 2/2019 | Haick et al. | |
| 2019/0308880 A1* | 10/2019 | Tour | B33Y 10/00 |
| 2020/0150075 A1* | 5/2020 | Nayak | G01N 27/3278 |
| 2020/0244243 A1 | 7/2020 | Cullinan et al. | |
| 2020/0292487 A1 | 9/2020 | Stowell et al. | |
| 2021/0172904 A1* | 6/2021 | Stowell | G01N 27/4141 |

FOREIGN PATENT DOCUMENTS

| | | | | |
|---|---|---|---|---|
| CN | 103373727 B | * | 11/2016 | ............ B82Y 30/00 |
| CN | 106198453 A | * | 12/2016 | ......... G01N 21/4133 |
| CN | 106324057 A | * | 1/2017 | ......... G01N 27/3278 |
| CN | 206096442 U | * | 4/2017 | |
| CN | 106783236 A | * | 5/2017 | |
| CN | 104677879 B | | 6/2017 | |
| CN | 105954592 B | * | 8/2017 | |
| CN | 107078548 A | * | 8/2017 | ............ B60L 53/12 |
| CN | 107082414 A | * | 8/2017 | .......... C01B 31/043 |
| CN | 107134479 A | * | 9/2017 | |
| CN | 107251380 A | * | 10/2017 | ............ H02J 15/00 |
| EP | 3067313 A1 | * | 9/2016 | |
| JP | WO2005088753 A1 | * | 8/2007 | |
| WO | 2000/014518 A1 | | 3/2000 | |
| WO | WO-2013059107 A1 | * | 4/2013 | ............ B82Y 30/00 |
| WO | WO-2013162470 A1 | * | 10/2013 | ............ B82Y 15/00 |
| WO | 2015/083073 A1 | | 6/2015 | |
| WO | WO-2017156297 A2 | * | 9/2017 | |
| WO | 2019/136181 A1 | | 7/2019 | |

OTHER PUBLICATIONS

Li et al. ("Three-Dimensional Mesoporous Graphene Aerogel-Supported SnO2 Nanocrystals for High-Performance NO2 Gas Sensing at Low Temperature"; University of Chinese Academy of Sciences, Beijing; 2015; pp. 1638-1645).*

Dossi et al., "An electrochemical gas sensor based on paper supported room temperature ionic liquids", Lab on a Chip, vol. 12, No. 1, Suppl. 1, Part 3, Feb. 2012, pp. 153-158.

International Search Report and Written Opinion dated Apr. 26, 2019 for PCT Patent Application No. PCT/US2019/012224, 9 pages.

Potyrailo, Radislav A., et al., "Multivariable MHz and GHz Wireless Chem/Bio Sensors for Environmental, Industrial, and Security Applications," IMCS May 2012, The 14th International Meeting on Chemical Sensors, pp. 399-402.

Sekhar et al., "Chemical Sensors for Environmental Monitoring and Homeland Security," The Electrochemical Society Interface, Winter 2010, pp. 35-40.

Singh, G., et al., "ZnO decorated luminescent graphene as a potential gas sensor at room temperature", Carbon, vol. 50, avail. from ScienceDirect on Sep. 1, 2011, pp. 385-394.

(56) References Cited

OTHER PUBLICATIONS

Skryshevsky et al., "Impedance spectroscopy of single graphene layer at gas adsorption," Phys. Status Solidi A, vol. 212, No. 9, pp. 1941-1945 (Apr. 2015).
Wang et al., "A Review on Graphene-Based Gas/Vapor Sensors with Unique Properties and Potential Applications," Nano-Micro Lett. Jul. 2015, 8(2): pp. 95-119.
Extended European Search Report issued in EP Appl. No. 21757136.3 (PCT/US2021/019110) dated Feb. 2, 2024; 11 pages.
Olariu, M. et al., "Electrostimulated Desorption Hydrogen Sensor Based on Onion-Like Carbons as a Sensing Element", Journal of Electronic Materials; Springer US, New York; vol. 47, No. 11; Aug. 3, 2018; pp. 6476-6483.

* cited by examiner

| Sensor | Carbon Recipe | TATP (10ppm) | DNT (200ppb) | H₂S (10 ppm) | Toluene (188 ppm) | Ammonia (62 ppm) | Ethanol (775 ppm) | Acetone (1000 ppm) | DMF (10 ppm) | Ethyl Acetate (400 ppm) |
|---|---|---|---|---|---|---|---|---|---|---|
| 1 | Cobalt Oxide (Co₂O3) decorated CNO | 9.262 | -1.196 | -2.290 | -1.573 | -4.200 | -1.193 | -0.73535 | -0.734 | -0.915 |
| 2 | Thermogravimetric Jet-Milled (TG-JM) | 1.810 | -2.471 | 0.711 | -0.757 | -1.912 | -0.639 | -0.4782 | -3.445 | -3.386 |
| 3 | Silver (Ag) decorated DXR | -6.105 | -4.0791 | -1.007 | -6.459 | -16.398 | -5.380 | -5.97174 | -6.327 | -1.464 |
| 4 | Undecorated Carbon Nano-Onions (CNOs) | 0.0183 | -3.478 | -6.740 | 0.093 | -0.264 | -2.666 | -0.59074 | -0.741 | -0.375 |
| 5 | Iron Oxide (Fe₂O3) decorated DXR | 0.685 | 0.953 | 0.388 | 1.261 | 0.523 | -0.008 | 0.095819 | 0.090 | -0.283 |
| 6 | Platinum (Pt) decorated DXR | -0.334 | 0.272 | 0.952 | 0.198 | -1.123 | -1.050 | -0.72308 | -0.198 | -0.156 |
| 7 | Palladium (Pd) Decorated Anvel (A25) | -0.589 | -0.193 | 1.736 | -0.297 | -0.980 | -0.469 | -0.49391 | -0.437 | -0.369 |
| 8 | Amine Functionalized TG-JM | -0.109 | -0.076 | 2.091 | -1.093 | -0.295 | -0.690 | -0.91877 | -0.454 | -0.646 |

*Figure 10A*

| Sensor No. | Corresponding Carbon Recipe |
|---|---|
| 1 | Carbon #29 |
| 2 | TG JM (thermal graphene jet milled; thermal reactor carbon unfunctionalized) |
| 3 | Carbon #19 |
| 4 | CNO (carbon nanoonion; thermal reactor carbon unfunctionalized) |
| 5 | Carbon #16 |
| 6 | Carbon #1 (may alternatively be Pt-anvel) |
| 7 | Carbon #6 |
| 8 | 1,3-diaminonaphthalene complexed to TG-JM (this is an organically modified carbon). |

SENSING DEVICE FOR DETECTING ANALYTES IN BATTERIES

CROSS-REFERENCE TO RELATED APPLICATIONS

This patent application is a continuation-in-part application and claims priority to U.S. patent application Ser. No. 16/887,293 entitled "RESONANT GAS SENSOR" filed on May 29, 2020, now U.S. Pat. No. 11,137,368, which claims priority to U.S. Provisional Patent Application No. 62/815,927 entitled "RESONANT GAS SENSOR" filed on Mar. 8, 2019 and is a continuation-in-part application of U.S. patent application Ser. No. 16/706,542 entitled "RESONANT GAS SENSOR" filed on Dec. 6, 2019, now U.S. Pat. No. 10,955,378, which is a continuation application of U.S. patent application Ser. No. 16/239,423 entitled "RESONANT GAS SENSOR" filed on Jan. 3, 2019, now U.S. Pat. No. 10,502,705, which claims priority to U.S. Provisional Patent Application No. 62/613,716 entitled "VOLATILES SENSOR" filed on Jan. 4, 2018. This patent application also claims priority to U.S. Provisional Patent Application No. 62/979,095 entitled "MULTIVARIATE IMPEDANCE SPECTROSCOPY SENSING" filed on Feb. 20, 2020, and to U.S. Provisional Patent application No. 63/088,541 entitled "CHEMICALLY-FUNCTIONALIZED CARBON-BASED RESONANT IMPEDANCE SPECTROSCOPY SENSOR ARRAYS" filed on Oct. 7, 2020, all of which are assigned to the assignee hereof. The disclosures of all prior applications are considered part of and are incorporated by reference in this patent application in their respective entireties.

TECHNICAL FIELD

This disclosure relates generally to detecting analytes, and, more particularly, to increasing the accuracy of analyte sensing devices.

DESCRIPTION OF RELATED ART

Chemical sensors operate by generating a signal in response to the presence of a particular chemical. Conventional analyte sensors typically require relatively high power energy sources to detect relatively low concentrations of analytes (such as less than 1 part per-billion (ppb)), which has made widespread adoption of such sensors impractical. Further improvements of chemical and vapor sensors are desirable.

SUMMARY

This Summary is provided to introduce in a simplified form a selection of concepts that are further described below in the Detailed Description. This Summary is not intended to identify key features or essential features of the claimed subject matter, nor is it intended to limit the scope of the claimed subject matter.

One innovative aspect of the subject matter described in this disclosure may be implemented as a sensing device for detecting analytes. The sensing device may include a substrate and a sensor array. The sensor array may be arranged on the substrate, and may include a plurality of carbon-based sensors. In some implementations, a first carbon-based sensor disposed between a first pair of electrodes may be configured to detect a presence of each analyte of a first group of analytes, and a second carbon-based sensor disposed between a second pair of electrodes may be configured to detect a presence of each analyte of a second group of analytes, where the second group of analytes is a subset of the first group of analytes. In some instances, the first group of analytes may include at least twice as many different analytes as the second group of analytes. In some implementations, the first carbon-based sensor may be configured to generate a first output signal in response to detecting the presence of one or more analytes of the first group of analytes, and the second carbon-based sensor may be configured to generate a second output signal in response to confirming the presence of the one or more analytes detected by the first carbon-based sensor. In one implementation, the first and second output signals may be currents based at least in part on an alternating current applied to the first and second carbon-based sensors. In some instances, a ratio of the current of the first output signal and the alternating current may be indicative of a concentration of at least one of the detected analytes, and a ratio of the current of the second output signal and the alternating current may be indicative of a concentration of at least one of the confirmed analytes.

In other implementations, the first and second output signals may be indicative of the impedances of the first and second carbon-based sensors, respectively. In some aspects, the first output signal may indicate a change in impedance of the first carbon-based sensor caused by exposure to one or more analytes of the first group of analytes, and the second output signal may indicate a change in impedance of the second carbon-based sensor caused by exposure to one or more analytes of the second group of analytes. In some other implementations, the first and second output signals may indicate frequency responses of the first and second carbon-based sensors, respectively. In some instances, the frequency response of the first carbon-based sensor may be indicative of the presence or absence of each analyte of the first group of analytes, and the frequency response of the second carbon-based sensor may be indicative of the presence or absence of each analyte of the second group of analytes. The frequency responses may be based on electrochemical impedance spectroscopy (EIS) sensing or resonant impedance spectroscopy (RIS) sensing.

In various implementations, the first carbon-based sensor may be functionalized with a first material configured to react with each analyte of the first group of analytes, and the second carbon-based sensor may be functionalized with a second material configured to react only with the analytes of the second group of analytes. In some instances, the first material may be cobalt-decorated carbon nano-onions (CNOs) configured to detect a presence of one or more of triacetone triperoxide (TATP), toluene, ammonia, or hydrogen sulfide ($H_2S$), and the second material may be iron-decorated three-dimensional (3D) graphene-inclusive structures configured to confirm the presence of toluene.

The substrate may be paper, a flexible polymer, or other suitable material. In some implementations, the substrate and the sensor array may be integrated within a label configured to be removably printed onto a surface of a package or container. In some aspects, each of the carbon-based sensors may be printed on the substrate using a different carbon-based ink, and the pairs of electrodes may be printed on the substrate using an ohmic-based ink. In some instances, the first and second carbon-based sensors may be stacked on one another. In other instances, the first and second carbon-based sensor may be disposed next to one another.

In some implementations, each of the carbon-based sensors may include a plurality of different graphene allotropes.

In some aspects, the different graphene allotropes of a respective carbon-based sensor may include one or more microporous pathways or mesoporous pathways. Each of the carbon-based sensors may include a polymer configured to bind the plurality of different graphene allotropes to one another. The polymer may include humectants configured reduce a susceptibility of a respective carbon-based sensor to humidity.

Another innovative aspect of the subject matter described in this disclosure may be implemented as a sensing device for detecting analytes within a package or container. In various implementations, the sensing device may include a substrate, one or more electrodes, and a sensor array. The sensor array may be disposed on the substrate, and may include a plurality of carbon-based sensors coupled to the one or more electrodes. In some implementations, the carbon-based sensors may be configured to react with unique groups of analytes in response to an electromagnetic signal received from an external device. In some instances, the carbon-based sensors may be configured to resonate at different frequencies in response to the electromagnetic signal. Each of the one or more electrodes may be configured to provide an output signal indicating whether a corresponding carbon-based sensor detected one or more analytes in a respective group of the unique groups of analytes. In some instances, each output signal may indicate an impedance or reactance of the corresponding carbon-based sensor.

In addition, or in the alternative, a first frequency response of the first carbon-based sensor to the electromagnetic signal may be indicative of the presence or absence of the analytes of the first group of analytes within the package or container, and a second frequency response of the second carbon-based sensor to the electromagnetic signal may be indicative of the presence or absence of the analytes of the second group of analytes within the package or container. In some instances, the first frequency response may be based at least in part on exposure of the first carbon-based sensor to the electromagnetic signal for a first period of time, and the second frequency response may be based at least in part on exposure of the second carbon-based sensor to the electromagnetic signal for a second period of time that is longer than the first period of time. In some instances, the second period of time is at least twice as long as the first period of time. The first and second frequency responses may be based on resonant impedance spectroscopy (RIS) sensing.

In various implementations, a first carbon-based sensor may be functionalized with a first material configured to detect the presence of each analyte of a first group of analytes, and a second carbon-based sensor may be functionalized with a second material configured to detect the presence of each analyte of a second group of analytes. The second group of analytes may be a subset of the first group of analytes, and the second material may be different than the first material. In some aspects, the first group of analytes may include at least twice as many different analytes as the second group of analytes. In some instances, the first material may be cobalt-decorated carbon nano-onions (CNOs) configured to detect the presence of one or more of triacetone triperoxide (TATP), toluene, ammonia, or hydrogen sulfide ($H_2S$), and the second material may be iron-decorated three-dimensional (3D) graphene-inclusive structures configured to confirm the presence of toluene. In various implementations, a third carbon-based sensor may be functionalized with a third material configured to detect the presence of each analyte of a third group of analytes, where the third group of analytes may be another subset of the first group of analytes, and the third material may be different than the first and second materials.

In some implementations, at least two of the carbon-based sensors may be juxtaposed in a planar arrangement on the substrate. In other implementations, the carbon-based sensors may be stacked on top of one another in a vertical arrangement. For example, in one implementation, the carbon-based sensors may form a permittivity gradient. In some aspects, a single electrode may be configured to provide an output signal indicating whether the stacked carbon-based sensors detected one or more analytes. The single electrode may also be configured to provide the output signal to the external device.

The substrate may be paper, a flexible polymer, or other suitable material. In some implementations, the substrate and the sensor array may be integrated within a label that can be removably printed on a surface of the package or container. In some aspects, each of the carbon-based sensors may be printed on the substrate using a different carbon-based ink, and the one or more electrodes may be printed on the substrate using an ohmic-based ink. In some implementations, each of the carbon-based sensors may include a plurality of different graphene allotropes. In some aspects, the different graphene allotropes of a respective carbon-based sensor may include one or more microporous pathways or mesoporous pathways. Each of the carbon-based sensors may include a polymer configured to bind the plurality of different graphene allotropes to one another. The polymer may include humectants configured reduce a susceptibility of a respective carbon-based sensor to humidity.

Another innovative aspect of the subject matter described in this disclosure may be implemented as a sensing device for monitoring a battery pack. The sensing device may include a substrate and a plurality of carbon-based sensors disposed on the substrate. Each of the carbon-based sensors may be coupled between a corresponding pair of electrodes. In some implementations, the 3D graphene-based sensing materials of a first carbon-based sensor may be functionalized with a first material configured to detect a presence of each analyte of a first group of analytes, and the 3D graphene-based sensing materials of a second carbon-based sensor may be functionalized with a second material configured to detect a presence of each analyte of a second group of analytes. In some aspects, the second group of analytes is a subset of the first group of analytes, and the group of analytes may include at least twice as many different analytes as the second group of analytes. In some instances, the first and second carbon-based sensors may be stacked on top of one another. In other instances, the first and second carbon-based sensors may be disposed next to one another. In some implementations, the carbon-based sensors may be carbon-based inks printed on the substrate. In some instances, the first carbon-based sensor may be a first carbon-based ink, and the second carbon-based sensor may be a second carbon-based ink different than the first carbon-based ink.

The first carbon-based sensor may be configured to generate a first output signal in response to detecting the presence of one or more analytes of the first group of analytes, and the second carbon-based sensor may be configured to generate a second output signal in response to confirming the presence of the one or more analytes detected by the first carbon-based sensor. In some implementations, the sensing device may include an input terminal to receive an alternating current, and the first and second output signals may be currents based at least in part on the alternating current. In some instances, a first difference between the alternating current and the first output signal may be indicative of the presence or absence of one or more analytes of the first group of analytes, and a second difference between the alternating current and the second output signal may be indicative of the presence or absence of one or more analytes of the second group of analytes.

In other implementations, the first output signal may indicate a change in impedance of the first carbon-based sensor caused by exposure to one or more analytes of the first group of analytes, and the second output signal may indicate a change in impedance of the second carbon-based sensor caused by exposure to one or more analytes of the second group of analytes. In some instances, a relatively small impedance change of a respective carbon-based sensor may indicate an absence of a corresponding group of analytes, and a relatively large impedance change of the respective carbon-based sensor may indicate a presence of the corresponding group of analytes.

In some other implementations, the sensing device may include an antenna configured to receive an electromagnetic signal from an external device, and the first and second output signals may be frequency responses of the 3D graphene-based sensing materials of the first and second carbon-based sensors, respectively, to the electromagnetic signal. For example, the frequency response of the 3D graphene-based sensing materials of the first carbon-based sensor may be indicative of the presence or absence of one or more analytes of the first group of analytes, and the frequency response of the 3D graphene-based sensing materials of the second carbon-based sensor may be indicative of the presence or absence of one or more analytes of the second group of analytes. In some aspects, the frequency responses may be based on resonant impedance spectroscopy (RIS) sensing.

In various implementations, at least one of the output signals may indicate an operating mode of the battery pack. In some implementations, the at least one output signal may indicate a normal mode based on an absence of the analytes of the first group of analytes, may indicate a maintenance mode based on the presence of one or more analytes of the first group of analytes not exceeding a threshold level, or may indicate an emergency mode based on the presence of one or more analytes of the first group of analytes exceeding a threshold level. In addition, or in the alternative, the first output signal may be indicative of a concentration level of one or more analytes of the first group of analytes, and the second output signal may be indicative of a concentration level of one or more analytes of the second group of analytes.

In some implementations, the analytes of the first and second groups of analytes may include one or more volatile organic compounds (VOCs). The one or more volatile organic compounds (VOCs) include any one or more of carbon dioxide ($CO_2$), carbon monoxide (CO), nitrogen dioxide ($NO_2$), one or more hydrocarbons including methane ($CH_4$), ethylene ($C_2H_4$), ethane ($C_2H_6$), or propane ($C_3H_8$), one or more acids including hydrochloric acid (HCl) or hydrofluoric acid (HF), one or more fluorinated hydrocarbons including phosphorus oxyfluoride, hydrogen cyanide (HCN), one or more aromatics including benzene ($C_6H_6$), toluene ($C_7H_8$), ethanol ($C_2H_5OH$), hydrogen, carbonate based electrolytes including ethylene carbonate ($C_3H_4O_3$), dimethyl carbonate ($C_3H_6O_3$), propylene carbonate ($C_4H_3O_3$), or one or more reduced sulfur compounds including thiols having a form of R—SH. In some aspects, each of the 3D graphene-based sensing materials may be configured to adsorb the VOCs. In some aspects, each of the carbon-based sensors may include a plurality of different graphene allotropes. The plurality of different graphene allotropes of a respective carbon-based sensor may include one or more microporous pathways or mesoporous pathways.

Another innovative aspect of the subject matter described in this disclosure may be implemented as a container for storing one or more items. The container may include a surface defining a volume of the container and a label printed on the container. In various implementations, the label may include a substrate, a plurality of carbon-based sensors printed on the substrate, and one or more electrodes printed on the substrate. The carbon-based sensors may be collectively configured to detect a presence of one or more analytes within the container. In some implementations, each of the carbon-based sensors may be configured to react with a unique group of analytes in response to an electromagnetic signal received from an external device. The one or more electrodes may be coupled to at least some of the carbon-based sensors, and may be configured to provide one or more output signals indicating the presence or absence of the one or more analytes within the container. In some implementations, a first electrode coupled to the first carbon-based sensor may be configured to indicate the presence of one or more analytes of the first group of analytes, and a second electrode coupled to the second carbon-based sensor may be configured to confirm the presence of the analytes detected by the first carbon-based sensor. In some aspects, the carbon-based sensors may be configured to resonate at different frequencies in response to the electromagnetic signal.

In some implementations, a first carbon-based sensor may be functionalized with a first material configured to detect the presence of each analyte of a first group of analytes, and a second carbon-based sensor may be functionalized with a second material configured to detect the presence of each analyte of a second group of analytes, where the second group of analytes may be a subset of the first group of analytes. In some aspects, the first group of analytes may include at least twice as many different analytes as the second group of analytes. The second material may be different than the first material. For example, in one implementation, the first material may be cobalt-decorated carbon nano-onions (CNOs) configured to detect the presence of one or more of triacetone triperoxide (TATP), toluene, ammonia, or hydrogen sulfide ($H_2S$), and the second material may be iron-decorated three-dimensional (3D) graphene-inclusive structures configured to confirm the presence of toluene. For another example, a third carbon-based sensor may be functionalized with a third material configured to detect the presence of each analyte of a third group of analytes, where the third group of analytes is another subset of the first group of analytes, and the third material is different than the first and second materials.

In some implementations, each output signal may indicate a frequency response of a corresponding carbon-based sensor to the electromagnetic signal. In some instances, a first frequency response of the first carbon-based sensor to the electromagnetic signal may be indicative of the presence or absence of the analytes of the first group of analytes within the container, and a second frequency response of the second carbon-based sensor to the electromagnetic signal may be indicative of the presence or absence of the analytes of the second group of analytes within the container. The first frequency response may be based at least in part on exposure of the first carbon-based sensor to the electromagnetic signal for a first period of time, and the second frequency response may be based at least in part on exposure of the second carbon-based sensor to the electromagnetic signal for a second period of time that is longer than the first period of time. In some aspects, the second period of time is at least twice as long as the first period of time. The first and second frequency responses may be based on resonant impedance spectroscopy (RIS) sensing.

In various implementations, an antenna may be printed on the substrate and configured to drive a current through the carbon-based sensors in response to the electromagnetic signal. In some aspects, each output signal may indicate an impedance or reactance of a corresponding carbon-based sensor to the current. The impedance or reactance of the carbon-based sensors may be indicative of the presence or absence of the one or more analytes within the container. For example, the impedance or reactance of the first carbon-based sensor may be indicative of the presence or absence of an analyte of the first group of analytes, and the impedance or reactance of the second carbon-based sensor may be indicative of the presence or absence of an analyte of the second group of analytes. In some instances, at least two of the carbon-based sensors are juxtaposed in a planar arrangement on the substrate. In other instances, the carbon-based sensors are stacked on top of one another. In some aspects, the carbon-based sensors may form a permittivity gradient.

In some implementations, each of the carbon-based sensing materials may include a plurality of different graphene allotropes. In some aspects, the different graphene allotropes of a respective carbon-based sensor may include one or more microporous pathways or mesoporous pathways. Each of the carbon-based sensors may include a polymer configured to bind the plurality of different graphene allotropes to one another. The polymer may include humectants configured reduce a susceptibility of a respective carbon-based sensor to humidity.

Details of one or more implementations of the subject matter described in this disclosure are set forth in the accompanying drawings and the description below. Other features, aspects, and advantages will become apparent from the description, the drawings and the claims. Note that the relative dimensions of the following figures may not be drawn to scale.

BRIEF DESCRIPTION OF THE DRAWINGS

FIG. 10A shows an example sensor configuration, according to some implementations.

FIG. 10B shows an example sensor configuration, according to other implementations.

Like reference numbers and designations in the various drawings indicate like elements.

DETAILED DESCRIPTION

Figure 1:
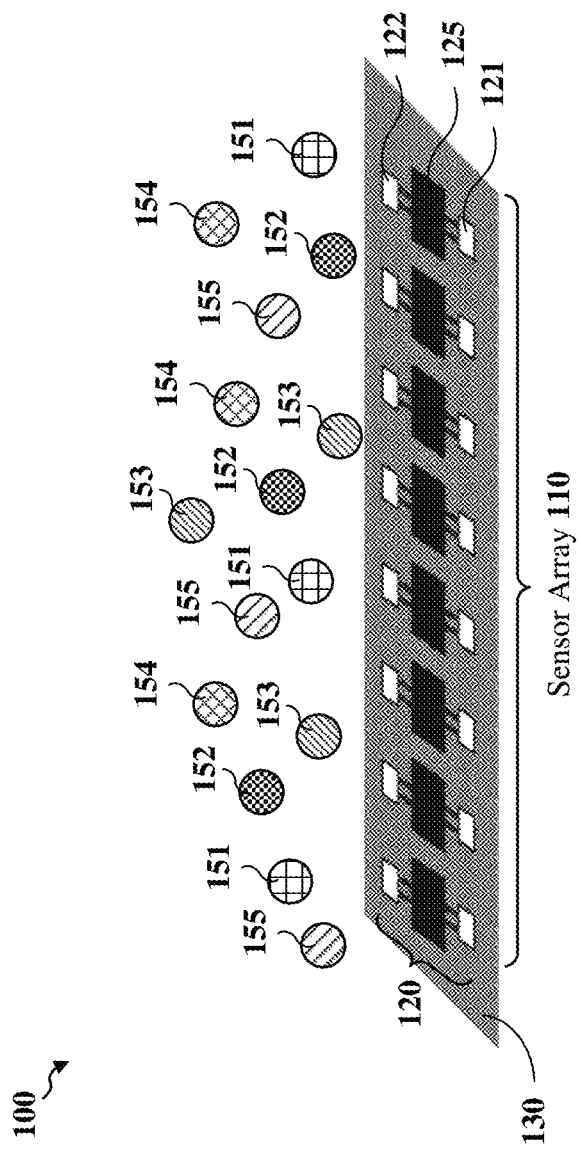
FIG. 1 shows an example sensing device configured to detect analytes, according to some implementations.

The following description is directed to some example implementations for the purposes of describing innovative aspects of this disclosure. However, a person having ordinary skill in the art will readily recognize that the teachings herein can be applied in a multitude of different ways. The described implementations can be implemented in any environment to detect the presence of a plurality of different analytes within or near any device, battery pack, package, container, structure, or system that may be susceptible to analytes. Moreover, implementations of the subject matter disclosed herein can be used to detect the presence of any harmful or dangerous chemical, gas, or vapor. As such, the disclosed implementations are not to be limited by the examples provided herein, but rather encompass all implementations contemplated by the attached claims. Additionally, well-known elements of the disclosure will not be described in detail or will be omitted so as not to obscure the relevant details of the disclosure.

Batteries typically include a plurality of electrochemical cells that can be used to power a wide variety of devices including, for example, mobile phones, laptops, and electric vehicles (EVs), factories, and buildings. When batteries are exposed to harsh environmental conditions or become damaged, toxic chemicals and vapors within the electrochemical cells may leak from the battery's casing and pose serious health and safety risks. When released from a battery, these toxic chemicals and vapors can cause respiratory problems, allergic reactions, and may even explode. The chemicals typically used in the cells of Lithium-ion batteries may be particularly dangerous due to their high reactivities and susceptibility to explosion when inadvertently released from the battery casing. As such, there is a need to quickly and accurately determine whether a particular battery or battery pack is leaking such toxic chemicals or vapors. Moreover, when the presence of one or more analytes (or other toxic chemicals or vapors) is detected, it may be desirable to determine the concentration of such analytes. It may also be desirable to predict battery failure and/or to determine the operational integrity of such batteries.

Various aspects of the subject matter disclosed herein relate to detecting a presence of one or more analytes in an environment. In accordance with various implementations of the subject matter disclosed herein, a sensing device may include a plurality of carbon-based sensors configured to the presence of a variety of different analytes. In some implementations, at least some of the carbon-based sensors may include different types of three-dimensional (3D) graphene-based sensing materials configured to react with different analytes or different groups of analytes. In some aspects, the sensing materials of different sensors may be functionalized with different materials, for example, to increase the sensitivity of each sensor to one or more corresponding analytes.

In some implementations, changes in the impedances of the sensors may be used to determine a presence of one or more analytes in a vicinity of the sensing device. In other implementations, changes in current flow through the sensors may be used to determine the presence of the one or more analytes in the vicinity of the sensing device. In some other implementations, frequency responses of the sensors may be used to determine the presence of the one or more analytes in the vicinity of the sensing device. In some aspects, the frequency responses of the sensors may be compared with one or more reference frequency responses corresponding to the one or more analytes to identify which analytes are present in the environment. In this way, the sensor systems disclosed herein can accurately detect the presence of a variety of different analytes in a given environment.

In one implementation, a first sensor may be configured to detect the presence of a relatively large number of different analytes, and one or more second sensors may be configured to confirm the presence of one or more analytes detected by the first sensor. Specifically, the first sensor may be configured to react with each analyte of a first group of analytes, and the one or more second sensors may be configured to react with corresponding second groups of analytes that are unique subsets of the first group of analytes. In some instances, the first sensor may be exposed to the surrounding environment for a relatively short period of time to provide an initial coarse indication of whether the analytes of the first group of analytes are present, and each of the second sensors may be exposed to the surrounding environment for a relatively long period of time to provide a fine indication of whether any of the analytes of the corresponding second group of analytes are present. For example, while the first sensor may be able to detect a greater number of analytes than any of the second sensors, configuring each of the second sensors to detect only one or two different analytes may increase the sensitivity of the second sensors to their respective "target" analytes, thereby increasing the accuracy with which the sensing device is able to detect the presence of various analytes. As such, when indications provided by the second sensors are used to confirm indications provided by the first sensor, the number of false positive indications decreases, which in turn increases overall accuracy of the sensing device.

Particular implementations of the subject matter described in this disclosure can be implemented to realize one or more of the following potential advantages. In some implementations, the sensing devices disclosed herein can not only detect the presence of a variety of analytes and other harmful chemicals and gases, but can also reduce the occurrence of false positives. Specifically, by using a first sensor to quickly detect a presence of one or more analytes of a group of analytes and using one or more second sensors to confirm the presence of analytes detected by the first sensor, aspects of the present disclosure can reduce the number of false positives indicated by the sensing device. This is in contrast to conventional analyte sensors that may not only be insensitive to differences between different analytes of a group of analytes and/or that do not employ a multi-tiered analyte detection system.

FIG. 1 shows an example sensing device 100 configured to detect analytes, according to some implementations. The sensing device 100 may include an array 110 of carbon-based sensors 120 disposed on a substrate 130. In some aspects, each of the carbon-based sensors 120 may include a carbon-based sensing material 125 disposed between a corresponding pair of electrodes 121-122, for example, as depicted in FIG. 1. In other aspects, the carbon-based sensors 120 may be coupled to only one electrode. The carbon-based sensors 120, as well as their respective carbon-based sensing materials 125, may be formed from any suitable materials that react to, or that can be configured to react to, a variety of different analytes. Reactions between the carbon-based sensors 120 and various analytes may be used to detect a presence of a particular analyte or a particular group of analytes. For example, the reactions may cause changes in current flow through one or more carbon-based sensors 120, may cause changes in the impedances or reactance of one or more carbon-based sensors 120, may produce unique or different frequency responses in one or more carbon-based sensors 120, or any combination thereof.

In the example of FIG. 1, a plurality of different analytes 151-155 are in the presence of the sensing device 100. Although only five analytes 151-155 are shown in FIG. 1, the sensing device 100 can detect a greater number of different analytes. In some aspects, the analytes 151-155 can include any vapor phase and/or fluidic composition including one or more volatile organic compounds (VOCs) such as (but not limited to) carbon dioxide ($CO_2$), carbon monoxide (CO), nitrogen dioxide ($NO_2$), one or more hydrocarbons including methane ($CH_4$), ethylene ($C_2H_4$), ethane ($C_2H_6$), or propane ($C_3H_8$), one or more acids including hydrochloric acid (HCl) or hydrofluoric acid (HF), one or more fluorinated hydrocarbons including phosphorus oxyfluoride, hydrogen cyanide (HCN), one or more aromatics including benzene ($C_6H_6$), toluene ($C_7H_8$), ethanol ($C_2H_5OH$), hydrogen, or one or more reduced sulfur compounds including thiols having a form of R—SH.

In some implementations, the carbon-based sensors 120 may include carbon particulates or 3D graphene structures that react with (or that can be configured to react with) analytes associated with batteries, for example, to determine whether a particular battery is leaking analytes that may be harmful or dangerous. In other implementations, the carbon-based sensors 120 may include carbon particulates or 3D graphene structures that react with (or that can be configured to react with) a group of analytes deemed to be harmful or dangerous, either individually or in combination with each other. For example, the carbon-based sensors 120 may be configured to produce detectable reactions when exposed to acetone and hydrogen peroxide to detect a presence of acetone peroxide (which is highly explosive). For another example, one or more of the carbon-based sensors 120 may be configured to detect a presence of triacetone triperoxide (TATP) or tri-cyclic acetone peroxide (TCAP), which are trimers for acetone peroxide.

In some implementations, each of the sensors 120 may be configured to react with a unique group of analytes. In some aspects, the sensors 120 may be functionalized with different materials configured to detect different analytes or different groups of analytes. In one implementation, a first sensor of the sensor array 110 may be functionalized with a first material configured to detect a presence of a first group of analytes, and one or more second sensors of the sensor array 110 may be functionalized with second materials configured to detect a presence of one or more corresponding second groups of analytes, where the second materials are different than each other and are different than the first material, and the second groups of analytes are unique subsets of the first group of analytes. For example, the first sensor may be configured to detect each of the five analytes 151-155, while each of the second sensors may be configured to detect only one of the five analytes 151-155. The first sensor may sense the environment for a relatively short period of time to provide a coarse detection of any of the analytes 151-155, and each of the second sensors may sense the environment for a relatively long period of time to confirm the presence of a respective one of the five analytes 151-155. In this way, the one or more second sensors 120 may be used to verify the detection of various analytes by the first sensor 120, thereby reducing or even eliminating false positives.

In other implementations, the sensors 120 may be configured to react with overlapping groups of analytes. In some other implementations, the sensors 120 may be configured to react with the same or similar groups of analytes.

The substrate 130 may be any suitable material. In some instances, the substrate may be paper or a flexible polymer. In other instances, the substrate 130 may be a rigid or semi-rigid material such as, for example, a printed circuit board.

Figure 2:
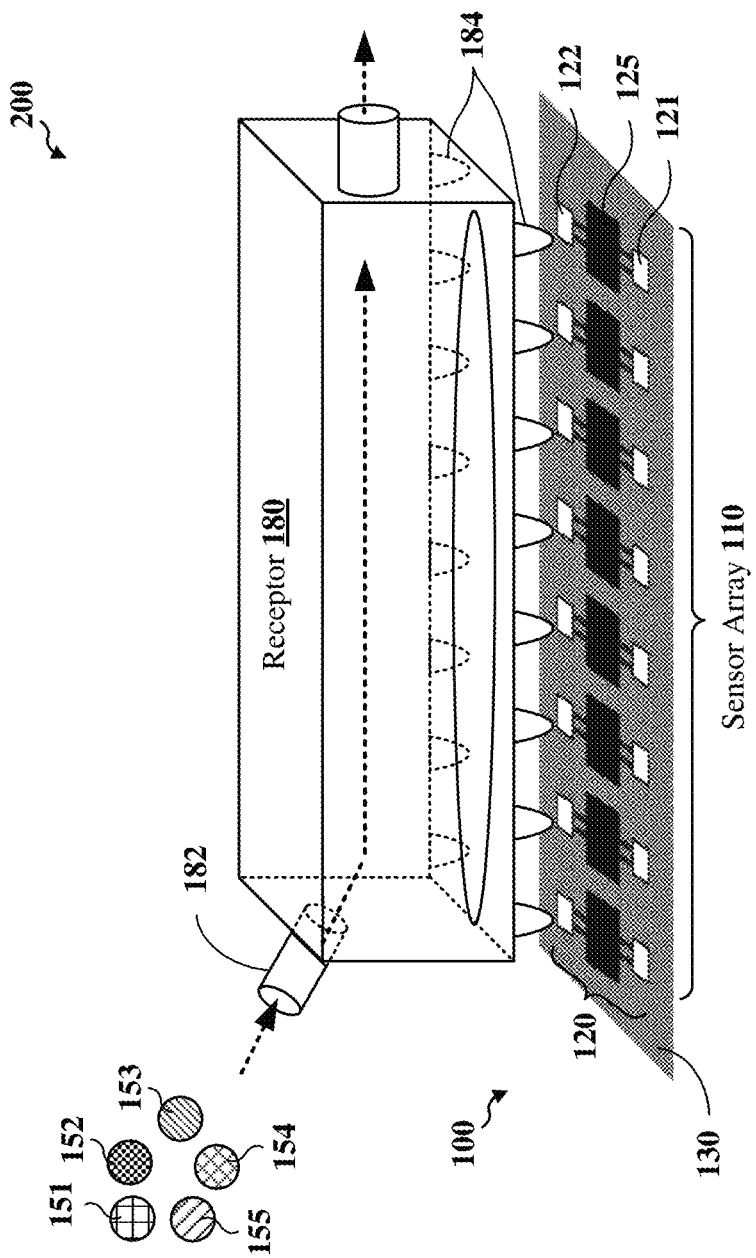
FIG. 2 is an illustration depicting the sensing device of FIG. 1 coupled to a receptor, according to some implementations.

FIG. 2 is an illustration 200 depicting the sensing device 100 of FIG. 1 coupled to a receptor 180, according to some implementations. The receptor 180 can be any suitable device, component, or mechanism capable or collecting, guiding, or steering analytes 151-155 present in a surrounding environment towards the sensing device 100. As shown, the receptor 180 includes an inlet 182 and a plurality of outlets 184. The inlet 182 may be configured to receive or attract the analytes 151-155 into the receptor 180, and the outlets 184 may be configured to steer the analytes 151-155 towards one or more exposed surfaces of the sensing device 100. In some implementations, each of the outlets 184 of the receptor 180 may be aligned with a corresponding sensor 120, for example, so that analytes 151-155 entering the receptor 180 can be released and exposed to each of the sensors 120 of the array 110. In this way, the receptor 180 may concentrate the analytes 151-155 on or near corresponding sensing materials 125 of the array 110, thereby increasing the likelihood of detection by the sensing device 100. For example, in instances for which the sensing device 100 is printed on a surface of a shipping package, a portion of the shipping package (e.g., a foldable flap) may be used as the receptor 180.

Figure 3:
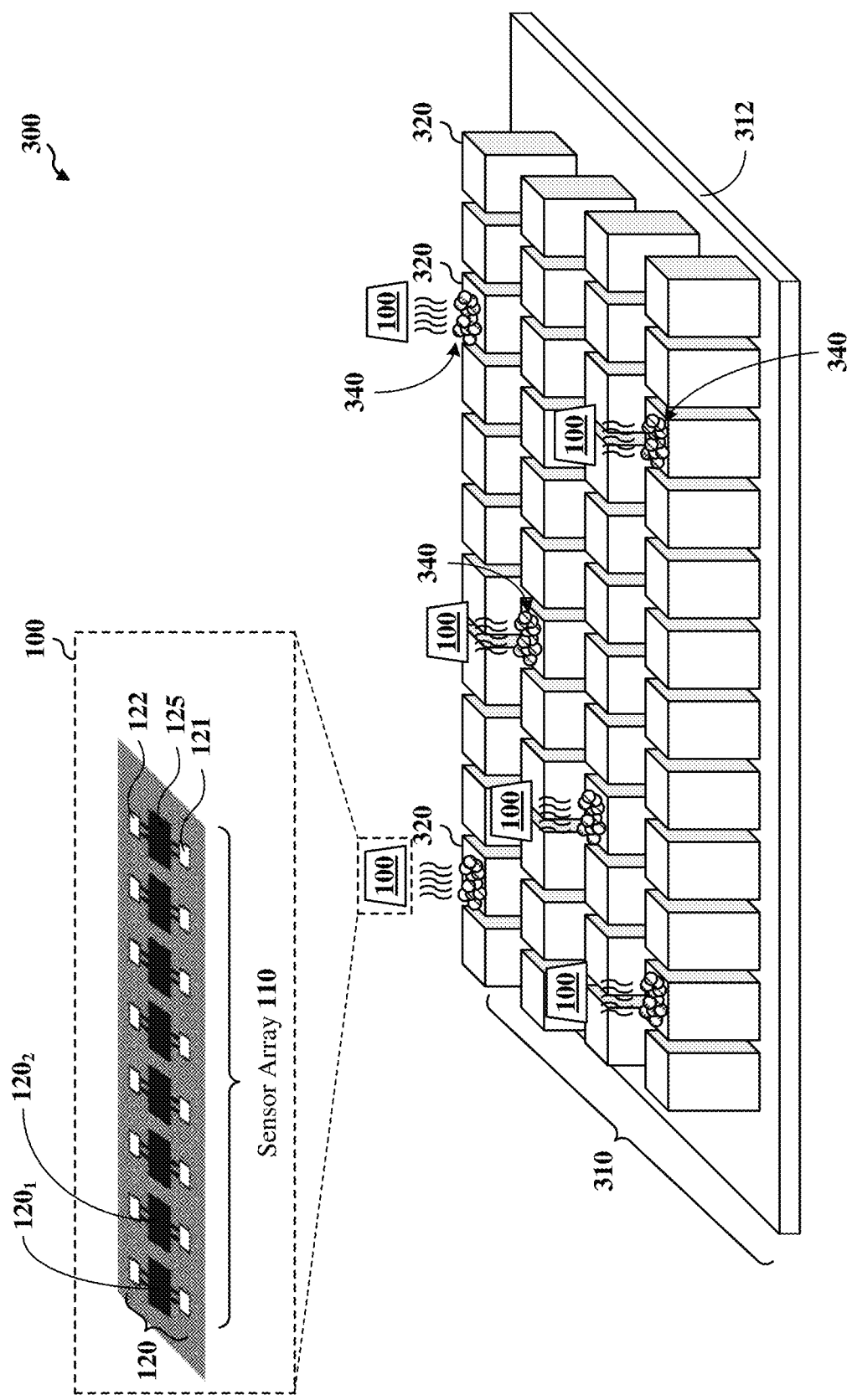
FIG. 3 is an illustration depicting the sensing device of FIG. 1 configured to detect analytes in a battery pack, according to some implementations.

FIG. 3 is an illustration 300 depicting the sensing device 100 of FIG. 1 configured to detect a presence of analytes within or near a battery pack 310, according to some implementations. The battery pack 310 is shown to include a plurality of battery cells 320 arranged as a planar array on a substrate 312. One or more sensing devices 100 may be positioned near or coupled to a corresponding number of the battery cells 320 of the battery pack 310. In some implementations, a subset of the battery cells 320 may be associated with the sensing devices 100 such that the number of sensing devices 100 is less than the number of battery cells 320, for example, as depicted in the example of FIG. 3. In other implementations, each of the battery cells 320 may be associated with or coupled to a corresponding sensing device 100. In some instances, the sensors 120 of a respective sensing device 100 may be stacked on top of one another (such as in a vertical arrangement). In other instances, the sensors 120 of the respective sensing device 100 may be disposed next to one another (such as in a planar arrangement).

The sensing devices 100 may be configured to detect a presence of analytes 340 leaked from one or more of the battery cells 320 of the battery pack 310 in a manner similar to that described above with reference to FIG. 1. Specifically, each of the sensors 120 may be coupled between a corresponding pair of electrodes 121-122 and may include a plurality of 3D graphene-based sensing materials 125 configured to detect a presence of certain analytes (such as the analytes 151-155 of FIG. 1). In some implementations, the sensing materials 125 within different sensors 120 may be configured to detect the presence of different analytes or different groups of analytes. For example, in some instances, the sensing materials 125 of a first sensor $120_1$ may be functionalized with a first material configured to detect a presence of each analyte of a first group of analytes, and the sensing materials 125 of a second sensor $120_2$ may be functionalized with a second material configured to detect a presence of each analyte of a second group of analytes, where the second group of analytes is a subset of the first group of analytes. In other implementations, the sensing materials 125 within different sensors 120 may be configured to detect the presence of the same analytes or the same group of analytes.

In various implementations, each of the sensors 120 within a respective sensing device 100 may be configured to provide an output signal in response to detecting the presence of one or more analytes. In some implementations, the output signal may be a current generated in response to an alternating current provided to the respective sensor 120. In some instances, a difference between the alternating current and the output signal may be indicative of the presence or absence of the one or more analytes of the first group of analytes. In other implementations, the output signal may indicate a change in impedance of the corresponding sensor 120 caused by exposure to the one or more analytes. In some instances, a relatively small impedance change of the sensor 120 may indicate an absence of the one or more analytes, and a relatively large impedance change of the sensor 120 may indicate a presence of the one or more analytes.

In some other implementations, one or more of the sensing devices 100 may include an antenna (not shown for simplicity) configured to receive an electromagnetic signal from an external device, and the output signals may be frequency responses of the sensing materials 125 to the electromagnetic signal. For example, the frequency response of the sensing materials 125 of the first sensor $120_1$ may be indicative of the presence or absence of the first group of analytes, and the frequency response of the sensing materials 125 of the second sensor $120_2$ may be indicative of the presence or absence of the second group of analytes. In some aspects, the frequency responses may be based on resonant impedance spectroscopy (RIS) sensing.

In various implementations, the output signals generated by each sensing device 100 may indicate an operating mode of a corresponding battery cell 320 of the battery pack 310. In some implementations, the output signals may indicate a normal mode for the corresponding battery cell 320 based on an absence of analytes, may indicate a maintenance mode for the corresponding battery cell 320 based on the presence of analytes not exceeding a threshold level, or may indicate an emergency mode for the corresponding battery cell 320 based on the presence of analytes exceeding the threshold level. The output signals may also indicate a concentration level of each analyte detected by the sensing device 100.

Figure 4:
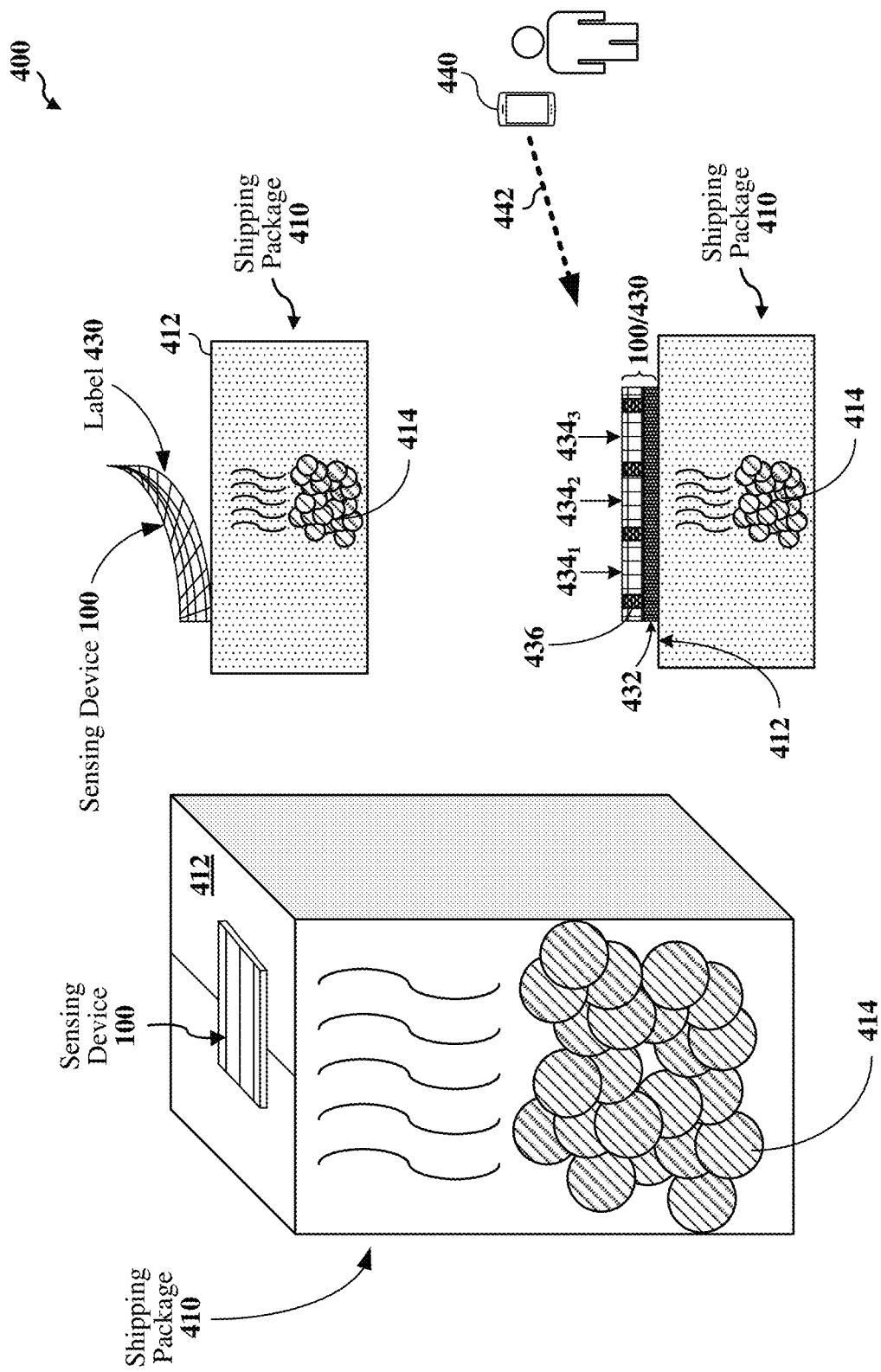
FIG. 4 is an illustration depicting the sensing device of FIG. 1 configured to detect analytes in a battery pack, according to some implementations.

FIG. 4 is an illustration 400 depicting the sensing device 100 of FIG. 1 configured to detect analytes in a shipping package 410, according to some implementations. The shipping package 410 is shown to include a surface 412 defining a volume within which one or more items (not shown for simplicity) can be contained. The defined volume of the shipping package 410 also includes a plurality of analytes 414 which can be, for example, one or more of the analytes 151-155 of FIG. 1. As shown, the sensing device 100 may be a label 430 that is printed onto the surface 412 of the shipping package 410. In various implementations, the label 430 may include a substrate 432, a plurality of carbon-based sensors 434 printed on the substrate, and one or more electrodes 436 printed on the substrate. The sensors 434, which may be examples of the carbon-based sensors 120 of FIG. 1, may be collectively configured to detect a presence of the analytes 414 within the shipping package 410.

In some implementations, each of the sensors 434 may be configured to react with a unique group of analytes in response to an electromagnetic signal 442 received from an external device 440. For example, a first sensor $434_1$ may be configured to detect the presence of a first group of analytes, and a second sensor $434_2$ may be configured to detect the presence of a second group of analytes that is a first subset of the first group of analytes. In one implementation, a third sensor $434_3$ may be configured to detect the presence of a third group of analytes that is a second subset of the first group of analytes. As discussed, the first sensor $434_1$ may be functionalized with a first material configured to react with the first group of analytes, the second sensor $434_2$ may be functionalized with a second material configured to react with the second group of analytes, and the third sensor $434_3$ may be functionalized with a third material configured to react with the third group of analytes. In this way, the second sensor $434_2$ may be used to confirm detection of the first subset of analytes by the first sensor $434_1$, and the third sensor $434_3$ may be used to confirm detection of the second subset of analytes by the first sensor $434_1$. In other implementations, one or more groups of sensors 434 may be configured to react with overlapping groups of analytes in response to the electromagnetic signal 442.

The electrodes 436, which may be examples of the electrodes 121-122 of FIG. 1, may be coupled to the sensors 434. In some implementations, each sensor 434 may be coupled between a corresponding pair of electrodes 436. The first electrode 436 of each electrode pair may be configured to receive the electromagnetic signal 442, and the second electrode 436 of each electrode pair may be configured to provide an output signal indicating whether the corresponding sensor 434 detected the presence of analytes.

In some implementations, each output signal may indicate a frequency response of a corresponding sensor 434 to the electromagnetic signal 442. For example, the frequency response of the first sensor $434_1$ may indicate the presence (or absence) of the first group of analytes within the shipping package 410, the frequency response of the second sensor $434_2$ may confirm the presence (or absence) of the second group of analytes, and the frequency response of the third sensor $434_3$ may confirm the presence (or absence) of the third group of analytes. In some instances, the first sensor $434_1$ may be exposed to the electromagnetic signal 442 for a relatively short period of time to provide a coarse indication of whether the analytes of the first group of analytes are present, and the second and third sensors $434_2$ and $434_3$ may be exposed to the electromagnetic signal 442 for a relatively long period of time to confirm indications of the presence of the second and third respective groups of analytes by the first sensor $434_1$. In this way, the sensors $434_1$-$434_3$ can collectively reduce the number of false positives indicated by the sensing device 100.

In at least some implementations, an antenna (not shown for simplicity) may be printed on the substrate 432 and configured to drive an alternating current through the sensors 434 in response to the electromagnetic signal 442. Because the sensors 434 may be functionalized with different materials that can have different electrical and/or chemical characteristics, the resulting sensor output currents may indicate the presence (or absence) of different analytes. For example, in some instances, each output signal may indicate an impedance or reactance of a corresponding sensor 434 to the alternating current. The impedance or reactance of each sensor 434 can be measured and compared with a reference impedance or reactance to determine whether one or more analytes associated with the sensor 434 are present in the shipping package 410. In some instances, the reference impedances or reactance may be determined by driving the alternating current through the sensors 434 in the absence of all analytes, and measuring the impedances or reactance of the output signals from the sensors 434.

In some aspects, the sensors 434 may be juxtaposed in a planar arrangement on the substrate 432. In other instances, the sensors 434 may be stacked on top of one another in a vertical arrangement. In some implementations, the sensors 434 may form a permittivity gradient.

As discussed, the analyte sensing devices disclosed herein can be integrated into a product or package, such as on a cardboard box, or food package. The analyte sensing devices disclosed herein can be placed adjacent to a product or package and can detect analytes on or within the product or package. For example, the analyte sensing device can be integrated into or placed adjacent to a scale that is used to weigh shipping containers, and the analyte sensing device can be used to detect analytes on or within any shipping package being weighed by the scale. As another example, the analyte sensing device can be integrated into or placed adjacent to a component of a vehicle that is used to transport shipping containers, such as within a mail truck, and the analyte sensing device can be used to detect analytes on or within any shipping package being transported by the vehicle. As still further examples, the analyte sensing device can be integrated into a conveyor belt or mounted onto a portion of a mechanical conveyance device. Additionally, or alternatively, the analyte sensing device can be integrated into handling equipment, such as a robot arm, or handling apparel, such as gloves, etc., and the analyte sensing device can be used to detect analytes on or within any shipping package being conveyed or handled.

In one implementation, a fan or a suction device, such as a vacuum pump, may be used to direct environmental gasses (which may include one or more analytes) towards the analyte sensing device and/or into an enclosure containing the analyte sensing device. For example, the analyte sensing device can be placed into an enclosure, and a fan or vacuum pump can draw the surrounding environmental gasses into the enclosure such that any analytes present in the environmental gasses are exposed to the analyte sensing device. In another example, the analyte sensing device may be placed adjacent to a set of objects, such as shipping packages, mousepads, or other products, and can monitor for the presence of one or more analytes.

Figure 5:
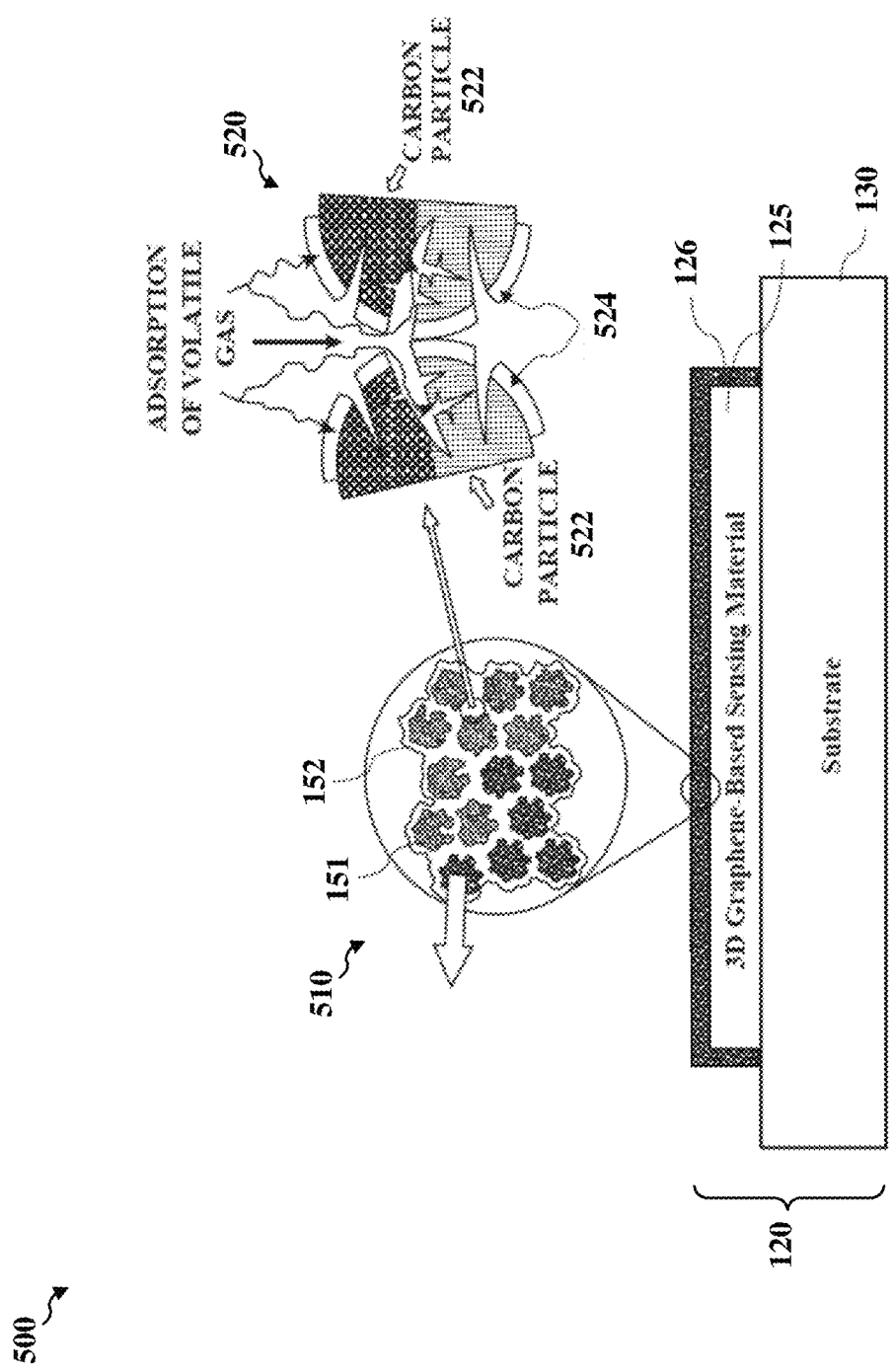
FIG. 5 is an illustration depicting reactions between one or more analytes and the sensing device of FIG. 1, according to some implementations.

FIG. 5 is an illustration 500 depicting example reactions between one or more analytes and the sensor 120 of FIG. 1, according to some implementations. As discussed, the sensor 120 may include 3D graphene-based sensing materials 125 disposed on the substrate 130, and the sensing materials 125 may be functionalized with a material 126 configured to detect the presence of analytes 151-152. In some implementations, the sensing materials 125 may include a plurality of different graphene allotropes having one or more microporous pathways or mesoporous pathways. Although not shown for simplicity, a polymer may bind the plurality of different graphene allotropes to one another. In some instances, the polymer may include humectants configured reduce the susceptibility of the carbon-based sensors to humidity.

As shown, analytes 151-152 may take a variety of paths to penetrate and react with the sensing material 125. Specifically, inset 510 depicts the analytes 151-152 being adsorbed by the functionalized material 126 and/or various exposed surfaces of the sensing material 125. Inset 520 depicts a carbon particulate 522 from which the sensing material 125 may be formed. In some instances, a reactive chemistry additive (such as a salt dissolved in a carrier solvent) may be deposited on and within exposed surfaces, pores and/or pathways of the particulate carbon 522. In some instances, the reactive chemistry additives may be incorporated into the particulate carbon 522 to increase the sensitivity of the sensor 120 to one or more specific analytes.

Figure 6:
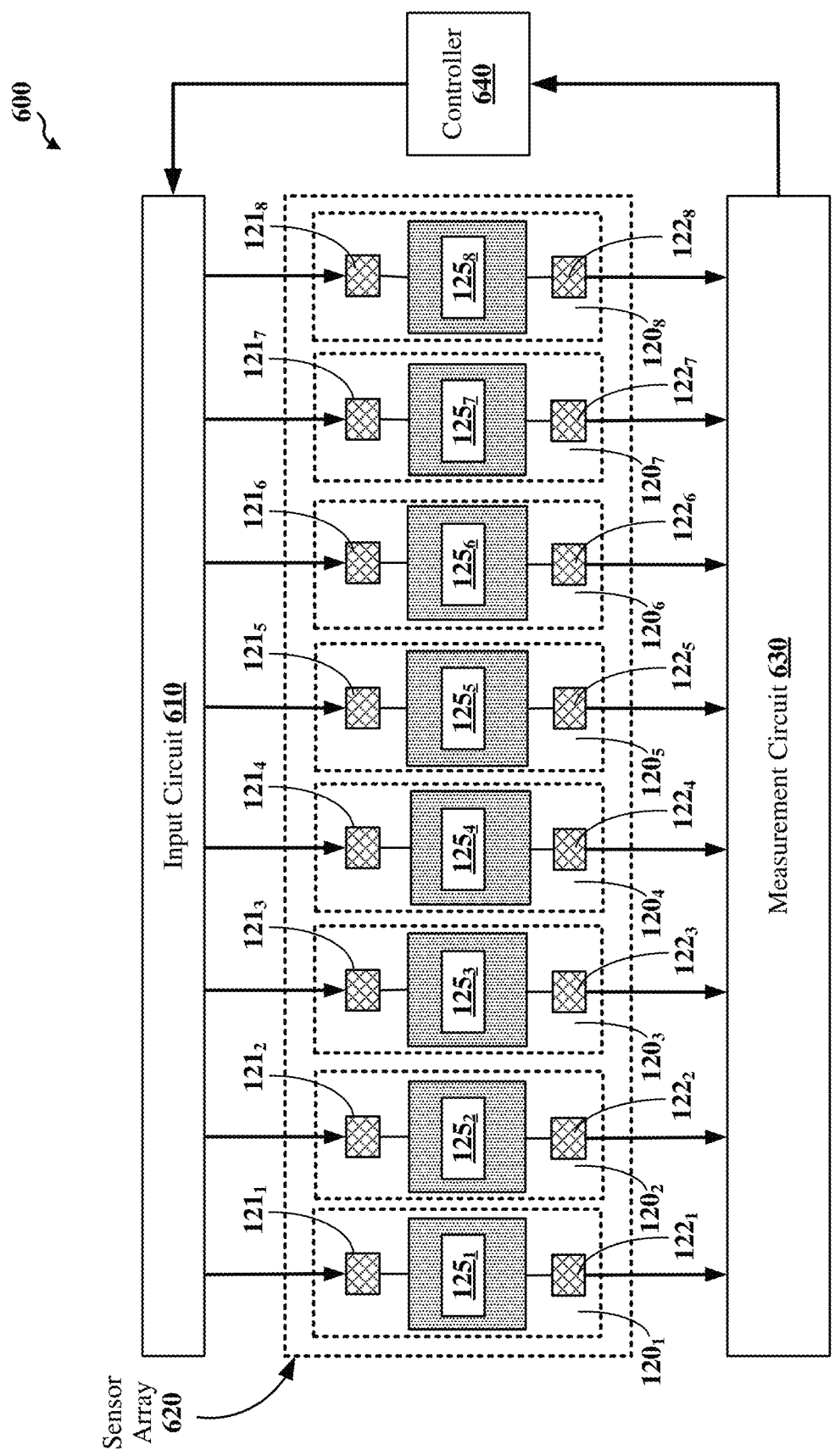
FIG. 6 is a block diagram of an analyte detection system that includes the sensing device of FIG. 1, according to some implementations.

FIG. 6 is a block diagram of an analyte detection system 600, according to some implementations. The analyte detection system 600 is shown to include an input circuit 610, a sensor array 620, a measurement circuit 630, and a controller 640. The input circuit 610 is coupled to the controller 640 and the sensor array 620, and may provide an interface through which currents, voltages, and electromagnetic signals can be applied to the sensor array 620. The sensor array 620, which may be one example of the sensor array 110 of FIG. 1, is shown to include eight carbon-based sensors $120_1$-$120_8$ coupled between respective pairs of electrodes $121_1$ and $122_1$ through $121_8$ and $122_8$. In some instances, each of the first electrodes $121_1$-$121_8$ may be coupled to a corresponding terminal of the input circuit 610, and each of the second electrodes $122_1$-$122_8$ may be coupled to a corresponding terminal of the measurement circuit 630. In other instances, each terminal of the input circuit 610 may be coupled to a corresponding group of the sensors $120_1$-$120_8$.

The controller 640 may generate an excitation signal or field from which current levels, voltage levels, impedances, and/or frequency responses of the carbon-based sensors $120_1$-$120_n$ can be measured or determined by the measurement circuit 630. For example, in some implementations, the controller 640 may be a current source configured to drive either a direct current or an alternating current through each of the sensors $120_1$-$120_8$. In other implementations, the controller 640 may be a voltage source that can apply various voltages across the sensors $120_1$-$120_8$ via corresponding pairs of electrodes 121 and 122. In some instances, the controller 640 can adjust the sensitivity of a respective sensor 120 to a particular analyte by changing the voltage applied across the respective sensor 120. For example, the controller 640 can increase the sensitivity of the respective sensor 120 by decreasing the applied voltage, and can decrease the sensitivity of the respective sensor 120 by increasing the applied voltage. In some other implementations, an antenna (not shown for simplicity) coupled to the sensor array 620 can receive one or more electromagnetic signals from an external device. In some aspects, the first electrodes $121_1$-$121_8$ may be configured to receive the electromagnetic signals.

As discussed, the sensors $120_1$-$120_8$ may include respective sensing materials $125_1$-$125_8$ that can be functionalized with different materials configured to react with and/or detect different analytes or different groups of analytes. In some implementations, the sensors $120_1$-$120_8$ may include cobalt in particulate form, and the sensing materials $125_1$-$125_8$ may include carbon nano-onions (CNOs). Specifically, active sites on exposed surfaces of the CNOs may, in some aspects, be functionalized (such as through surface modification) with solid-phase cobalt ($Co_{(S)}$)) (such as Co particles) and/or cobalt oxide ($Co_2O_3$), which reacts with available carbon on exposed surfaces of the CNOs. For example, the chemical reactions associated with using cobalt oxide to detect the presence of hydrogen peroxide ($H_2O_2$) may be expressed as:

$$2Co^{3+}_{2+}Pc + H_2O_2 \rightarrow 2Co^{2+}_{+}Pc + 2H^+ + O_2 \quad \text{(Eq. 1)}$$

$$2Co^{2+}_{+}Pc \rightarrow 2Co^{3+}_{2+}Pc + 2e^- \quad \text{(Eq. 2)}$$

$$H_2O_2 \rightarrow 2H^+ + O_2 + 2e^- \text{ (overall reaction)} \quad \text{(Eq. 3)}$$

In addition, or the alternative, cobalt-based functionalization may be used to detect TATP according to the following chemical reaction:

$$TATP + H^+ \rightarrow 3(CH_3)_2CO + 3H_2O_2 \quad \text{(Eq. 4)}$$

In other implementations, the presence of TATP may be detected based on the following steps or operations:
  adsorption of TATP (50 ppb) onto exposed carbon surfaces (300-700 $m^2/g$), which are acidic in nature by adding acid (such as HCl at an approximate 0.1 m concentration level). Example acid treatment levels include 10 mg carbon (C) corresponding to 100 mg HCl at 0.1 m diluted in a suitable carrier solvent. Over time, the adsorbed HCl evaporates and protonates hydroxyl and/or carboxylic groups on exposed carbon surfaces to leave such surfaces in a relatively acidic state;
  hydrolysis of TATP into acetone and peroxide;
  performance of peroxide oxidation shown by Eq. (1)-(3) above; and
  the generation of free electrons and associated observable changes in one or more electrical or chemical characteristics of the sensing device.

In some implementations, Cobalt decorated CNOs may provide the most selective and sensitive response to triacetone triperoxide (TATP) relative to other types of 3D graphene-based sensing materials. Applicant notes that since hydrogen peroxide has a chemical structure somewhat similar to triacetone triperoxide (TATP) or tri-cyclic acetone peroxide (TCAP), sensing devices configured to detect a presence of hydrogen peroxide can also be used to detect a presence of TATP.

The exact chemical reactivity and/or interactions between an analyte and exposed carbon surfaces of the materials $125_1$-$125_8$ may depend on the type of analyte and the structure or organization of the corresponding materials $125_1$-$125_8$. For example, certain analytes, such as hydrogen peroxide ($H_2O_2$) and TATP, may be detected by one or more oxidation-reduction ("redox") type chemical reactions with metals decorated onto exposed carbon surface of the sensing materials $125_1$-$125_8$. In some implementations, some of the sensing materials $125_1$-$125_8$ may be prepared or created to include free amines, which may react with electronic deficient nitroaromatic analytes, such as TNT and DNT.

The measurement circuit 630 may measure the output signals provided by the sensors $120_1$-$120_8$ to determine whether certain analytes are present in the surrounding environment. For example, when the sensor array 120 is pinged with an electromagnetic signal (e.g., received from an external device such as the device 440 of FIG. 4), the measurement circuit can measure the frequency responses of the sensors $120_1$-$120_8$, and compare the measured frequency responses with one or more reference frequency responses. If the measured frequency response of a sensor 120 matches a particular reference frequency response, then the measurement circuit 630 may indicate a presence of analytes associated with the particular reference frequency response. Conversely, if the measured frequency response of the sensor 120 does not match any of the reference frequency responses, then the measurement circuit 630 may indicate an absence of analytes associated with the particular reference frequency response.

For another example, application of an alternating current to the sensor array 120 may cause one or more electrical and/or chemical characteristics of the sensors $120_1$-$120_8$ to change (e.g., to increase or decrease). The measurement circuit 630 can detect the resultant changes in the electrical and/or chemical characteristics of the sensors $120_1$-$120_8$, and can determine whether certain analytes are present based on the changes. In some implementations, the measurement circuit 630 can measure the output currents of sensors $120_1$-$120_8$ caused by the alternating current, and can compare the measured output currents with one or more reference currents to determine whether certain analytes are present. Specifically, if the measured output current of a sensor 120 matches a particular reference current, then the measurement circuit 630 may indicate the presence of analytes associated with the particular reference current. Conversely, if the measured output current of the sensor 120 does not match any of the reference currents, then the measurement circuit 630 may indicate an absence of analytes associated with the particular reference current.

In other implementations, the measurement circuit 630 can measure the impedances or reactance of the sensors $120_1$-$120_8$ to the alternating current, and can compare the measured impedances or reactance with one or more reference impedances or reactance to determine whether certain analytes are present. Specifically, if the measured impedance or reactance of a sensor 120 matches a reference impedances or reactance, then the measurement circuit 630 may indicate the presence of analytes associated with the reference impedances or reactance. Conversely, if the measured impedance or reactance of the sensor 120 does not match any of the reference impedances or reactance, then the measurement circuit 630 may indicate an absence of analytes associated with the reference impedances or reactance.

Figure 7B:
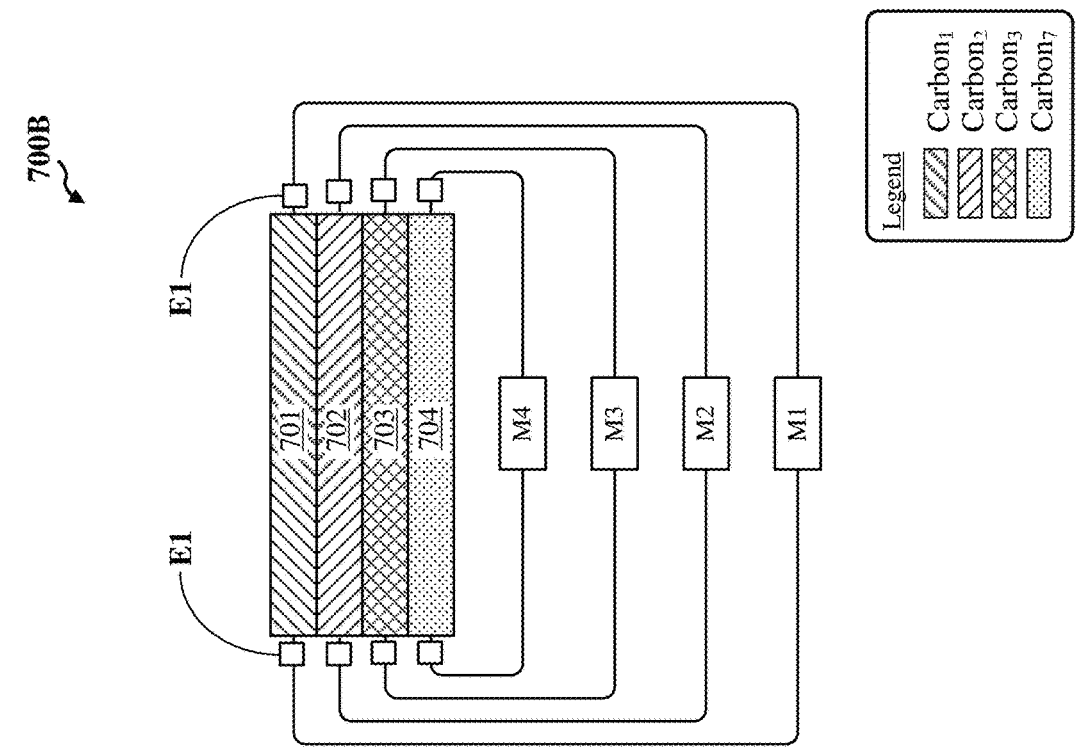
FIGS. 7A-7E show sensor arrays configured to detect analytes, according to various implementations.
Figure 7A:
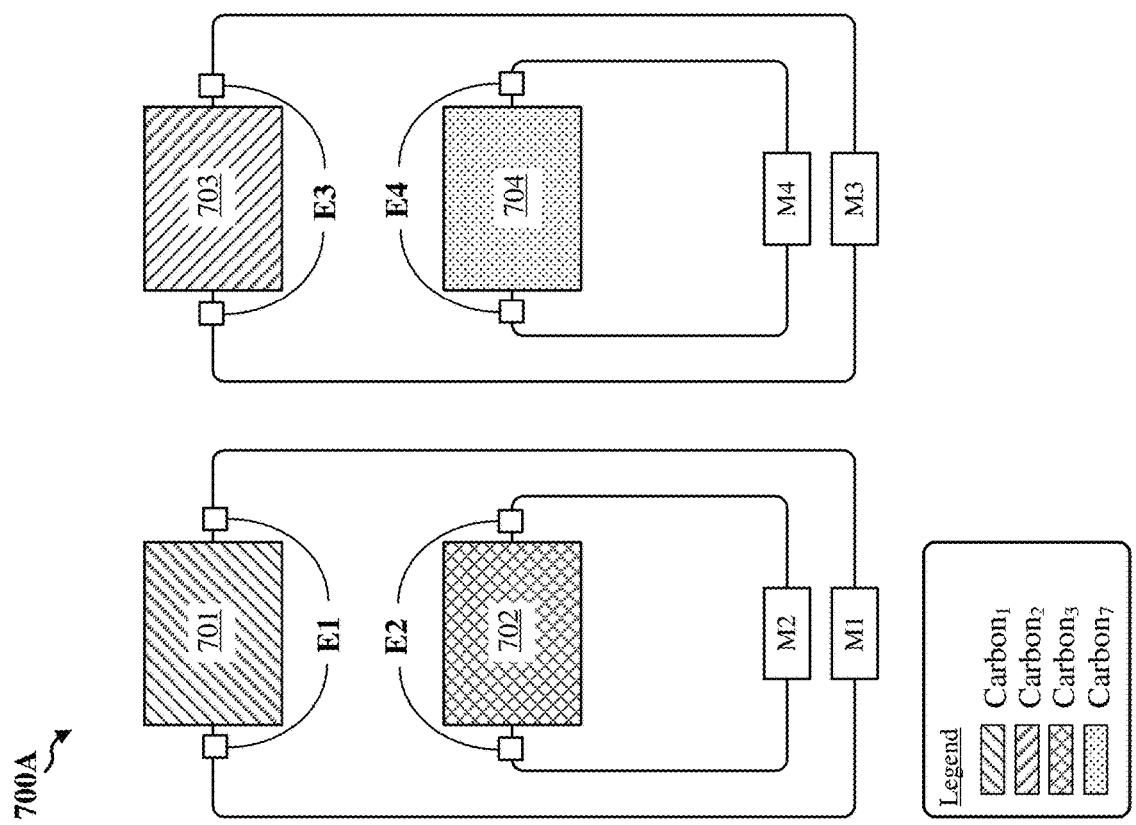

FIG. 7A shows another sensor array 700A, according to some implementations. As shown, the sensor array 700A includes a plurality of sensors 701-704 disposed in a planar arrangement, with each of the sensors 701-704 including a different carbon-based sensing material. In some aspects, the sensors 701-704 may be examples of the sensors 120 of FIGS. 1-3 and FIGS. 5-6. In other aspects, the sensors 701-704 may be examples of the sensors 434 of FIG. 4. Although the example 700A of FIG. 7A shows four sensors 701-704 arranged in a 2-row by 2-column array, in other implementations, the other numbers of sensors can be disposed in other suitable arrangements.

The sensors 701-704 may include routing channels between individual deposits of the carbon-based sensing materials. These routing channels may provide routes through which electrons can flow through the sensors 701-704. The resulting currents through the sensors 701-704 can be measured through ohmic contact with the respective electrode pairs E1-E4. For example, a measurement $M_1$ of the first sensor 701 can be taken via electrode pair E1, a measurement $M_2$ of the second sensor 702 can be taken via electrode pair E2, a measurement $M_3$ of the third sensor 703 can be taken via electrode pair E3, and a measurement $M_4$ of the fourth carbon-based sensor 704 can be taken via electrode pair E4.

In various implementations, each of the sensors 701-704 can be configured to react with and/or to detect a corresponding analyte or group of analytes. For example, the first sensor 701 can be configured to react with or detect a first group of analytes in a coarse-grained manner, and the second sensor 702 can be configured to react with or detect a subset of the first group of analytes in a fine-grained manner. In some instances, the sensors 701-704 can be printed onto a substrate using different carbon-based inks. Ohmic contact points can be used to capture the measurements $M_1$-$M_4$, either concurrently or sequentially.

FIG. 7B shows another sensor array 700B, according to some implementations. The sensor array 700B includes a plurality of carbon-based sensors 701-704 stacked on top of one another in a vertical or stacked arrangement. In some aspects, the sensors 701-704 may be examples of the sensors 120 of FIGS. 1-3 and FIGS. 5-6. In other aspects, the sensors 701-704 may be examples of the sensors 434 of FIG. 4. The sensors 701-704 (and their respective sensing materials) can be sequentially deposited upon one another to form the stacked array. In some instances, separators (not shown for simplicity) can be provided between the sensors 701-704. As discussed, the sensors 701-704 may be functionalized with different materials and/or may include different types of carbon-based sensing materials that can be printed in successive layers onto a substrate or label.

As the demand for low-cost analyte sensors continues to increase, it is increasingly important to reduce or even eliminate the need for electronic components in analyte sensors. For example, the high cost of electronic components typically found in conventional analyte sensors render their widespread deployment in shipping containers, packages, and envelopes impractical. As such, some implementations of the subject matter disclosed herein may provide a cost-effective solution to the long-standing problem of monitoring large numbers of shipping containers, packages, and envelopes for the presence of harmful chemicals and gases such as, for example, the various analytes described herein.

Figure 7C:
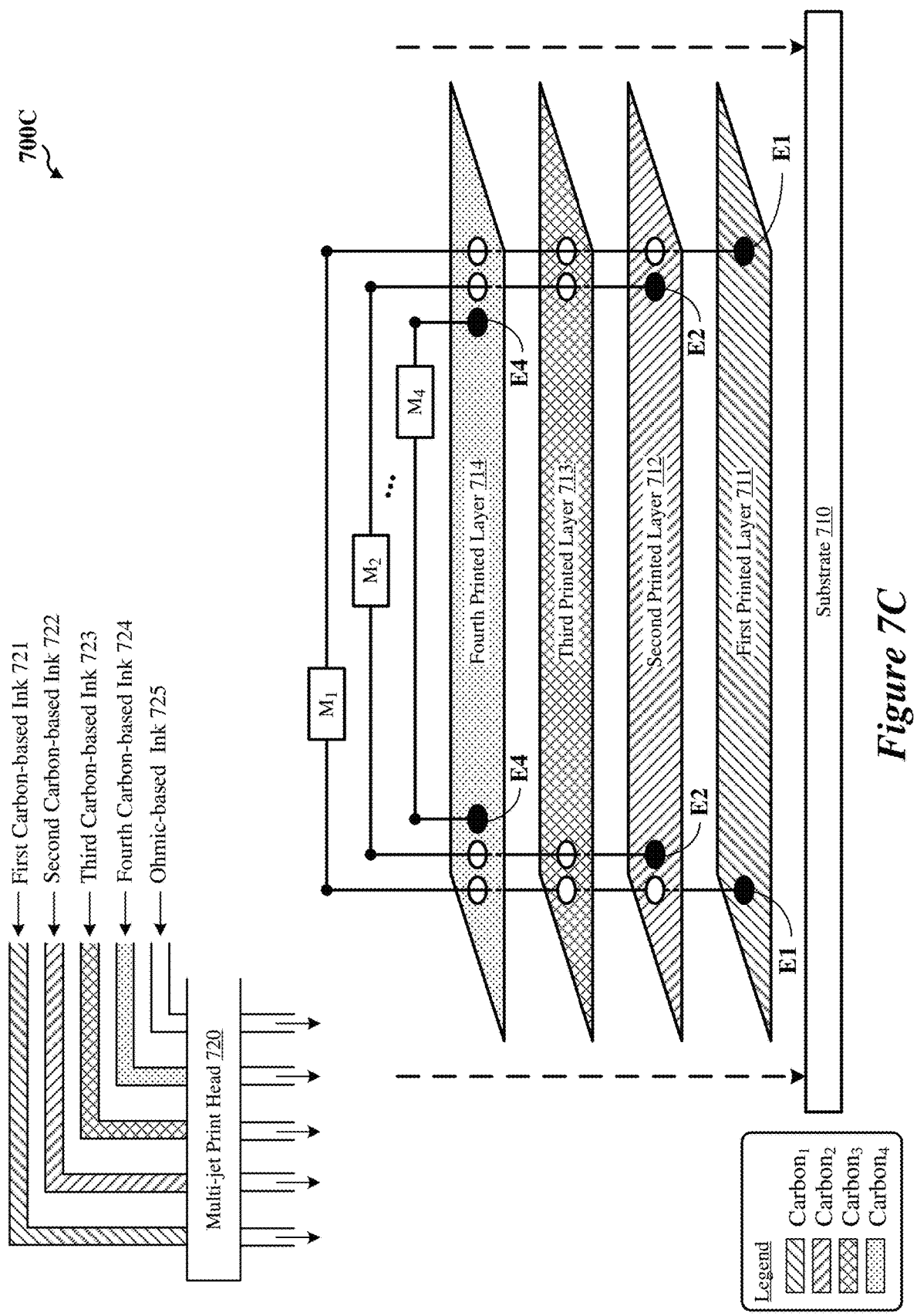

FIG. 7C is an illustration 700C depicting an ink-jet or bubble-jet print head 720 printing various sensing devices disclosed herein onto the surface of a shipping container, package, or envelope, according to some implementations. Specifically, the illustration 700C depicts a process by which multiple layers of different carbon-based sensing materials 711-714 can be printed onto a substrate 710. As shown, the print head 720 can print a first layer 711 of carbon-based sensing materials onto the substrate 710 using a first carbon-based ink 721, can print a second layer 712 of carbon-based sensing materials onto the substrate 710 using a second carbon-based ink 722, can print a third layer 713 of carbon-based sensing materials onto the substrate 710 using a third carbon-based ink 723, and can print a fourth layer 714 of carbon-based sensing materials onto the substrate 710 using a fourth carbon-based ink 724. In some instances, the carbon-based inks 721-724 may be different from one another, for example, such that the resulting sensing material layers 711-714 are configured to react with and/or detect different analytes or different group of analytes. The print head 720 can also print electrodes E1-E4 for the different sensing material layers 711-714, respectively, using an ohmic-based ink 725. Ohmic contacts can be printed onto the substrate 710 and/or portions of the sensing material layers 711-714 using multiple passes of the multi-jet print head 720. In some implementations, the sensing device may include vias through which the resulting electrodes E1-E4 can be accessed. In other implementations, other suitable mechanisms can be used to provide ohmic contacts for the electrodes E1-E4.

Figure 7D:
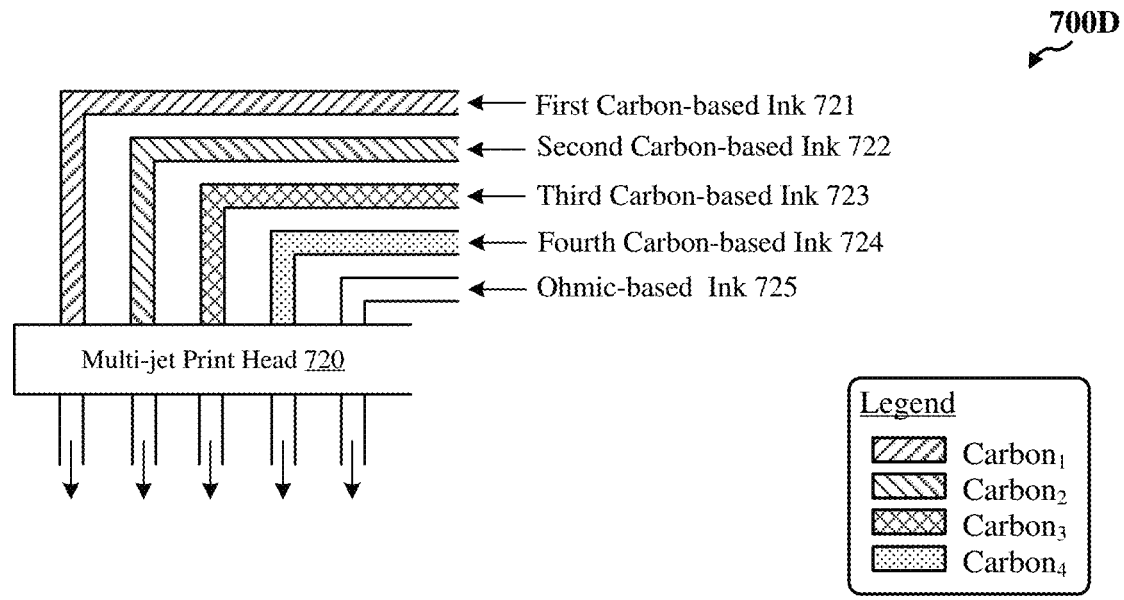
Figure 7D:
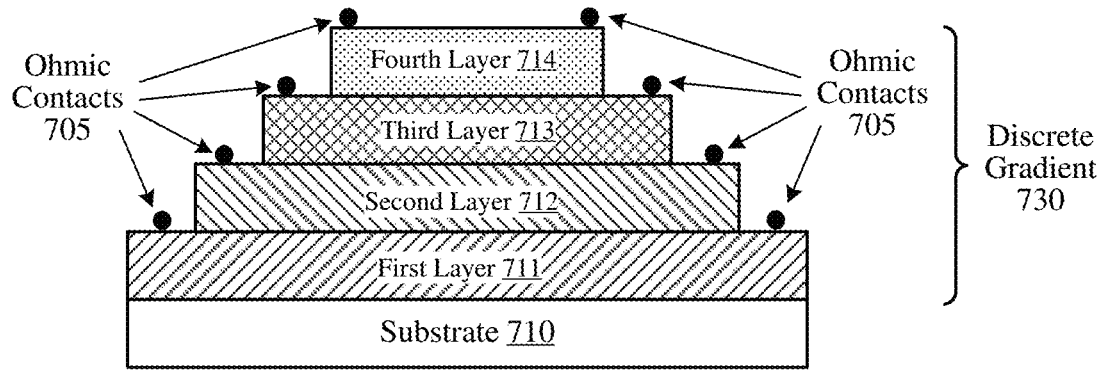

FIG. 7D is an illustration 700D depicting the print head 720 printing various sensing devices disclosed herein onto the surface of a shipping container, package, or envelope, according to other implementations. Specifically, the illustration 700D depicts a process by which multiple layers of different carbon-based sensing materials 711-714 can be printed onto a substrate 710 in a pyramid arrangement. The illustration 700D also depicts ohmic contacts 705 printed on the sensing material layers 711-714 using an ohmic-based ink 725. In some aspects, the different sizes and different exposed surface areas of the sensing material layers 711-714 may cause the respective sensors to have different electrical and/or chemical characteristics, which in turn may configured the respective sensors to react with and/or detect different types of analytes.

Further details pertaining to various carbon-based sensing materials, tunings, and calibration techniques that can be used to form carbon-based sensors disclosed herein are summarized below in Table 1.

can be controlled by a power control unit 751 and a wavelength control unit 752, respectively. In some implementations, adjusting the power level and/or wavelength of UV radiation can change the permittivity of each of the sensing material layers 711-714. That is, after bombarded with the UV radiation, each of the sensing material layers 711-714 may resonate at a different frequency. In some aspects, the different permittivity of the sensing material layers 711-714 may collectively a permittivity gradient 725. The permittivity gradient 725 may correspond to a stair shaped gradient 761, a linearly shaped gradient 762, or a curvilinearly shaped gradient 763.

Figure 8:
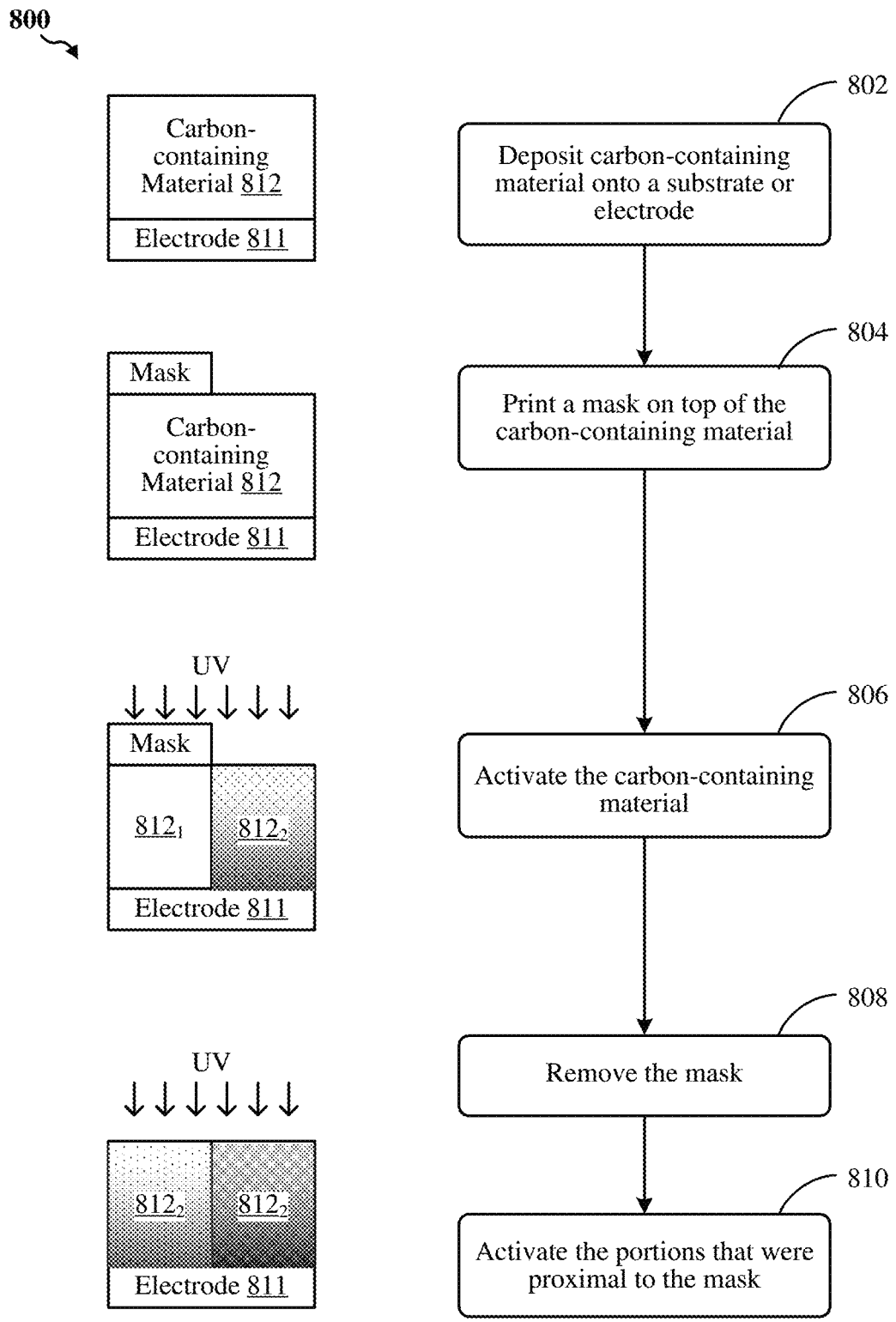
FIG. 8 shows a flow chart depicting an example operation for fabricating at least some of the sensing devices disclosed herein, according to some implementations.

FIG. 8 shows a flow chart 800 depicting an example operation for fabricating at least some of the sensing devices disclosed herein, according to some implementations. In various implementations, the permittivity of a carbon-based sensing material can be altered to cause a particular resonance signature in the carbon-based sensing material when exposed to certain analytes. In some cases, different portions of the carbon-based sensing material may be configured to have different permittivity values specifically selected to cause particular resonance frequencies and/or or resonance signatures. In particular, it is sometimes desired that a first portion of the carbon-containing material with a first permittivity that is tuned to resonate with a particular resonance signature when the first portion of the carbon-containing material has imbibed a first analyte of interest, whereas a second portion of the carbon-containing material has a second permittivity that is tuned to resonate with a particular resonance signature when the second portion of the carbon-containing material has imbibed a second analyte of interest.

Formation of different portions of the carbon-containing material having different permittivity values can be accomplished using a combination of masking and UV treatments.

TABLE 1

| Components | Tuning | Sensitivity | Calibration |
| --- | --- | --- | --- |
| Different carbon types and/or different carbon decorations | Select carbon functionalization materials to detect selected analytes | Surface area of carbon-based sensor | Response of the selected carbon functionalization materials to the selected analytes |
| Physical dimensions of the sensing material | Select size and/or aspect ratio of exposed portion of sensor | Surface area of carbon-based sensor | Sensitivity is based on physical dimensions and characteristics of carbon-based sensor |
| Adjacency or proximity to other carbon-based sensing materials | Select distance between sensors to reduce overlapping response signals | Select distance between sensors to reduce overlapping response signals | Calibrate based on test sample over a range conditions |
| Different permittivity of the different materials | Tune permittivity based on sensor material/functionalization | Select distance between sensors to reduce overlapping response signals | Calibrate based on test sample over a range conditions |

As discussed, different materials may resonate at different frequencies, and many materials may resonate at different frequencies depending on whether one or more certain analytes are present. In some implementations, the permittivity of carbon-based sensing materials described herein can be modified by exposing the materials to ultraviolet (UV) radiation.

Figure 7E:
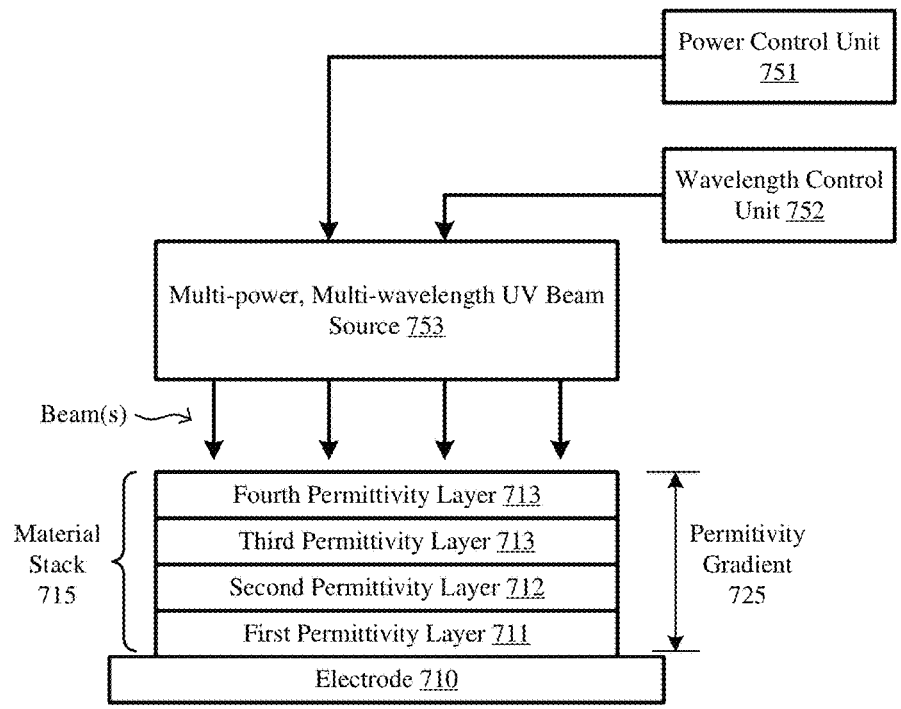
Figure 7E:
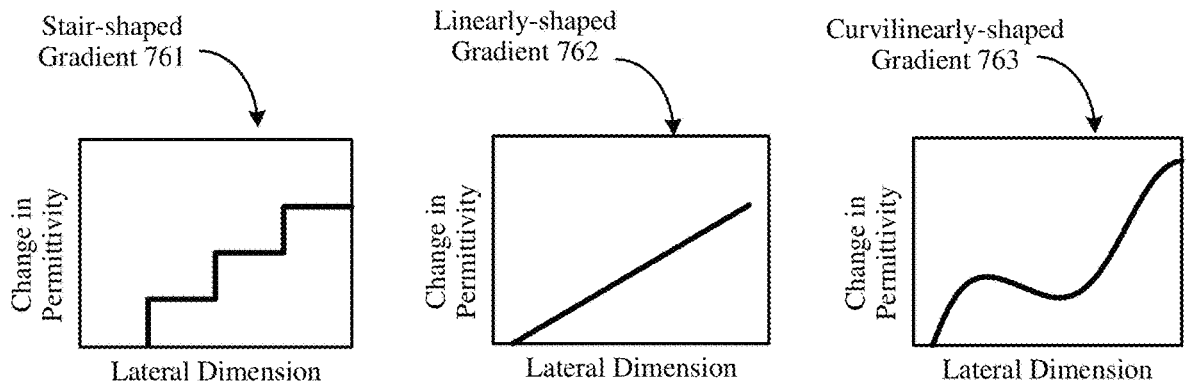

FIG. 7E is an illustration 700E depicting UV radiation emitted towards the sensor 701. As shown, a UV beam source 753 may be used to shower the sensor 701 with UV radiation. The power and wavelength of the UV radiation At block 802, a carbon-containing material is deposited onto a substrate or electrode 811. At block 804, a UV-opaque mask is deposited or printed on top the carbon-containing material. At block 806, the carbon-containing material is activated, for example, via bombardment by UV photons. This results in a first portion $812_1$ of the carbon-containing material having a first permittivity, and a second portion $812_2$ of the carbon-containing material having a second permittivity different than the first permittivity. At block 808, the mask can be washed away, ablated, or otherwise removed. Two or more of the resulting analyte-sensing devices can be used as a multi-element, multi-analyte sensor and/or as a high-sensitivity analyte sensor. In addition, or in the alternative, the resulting analyte-sensing devices can be exposed to an additional bombardment of UV photons at block 810, for example, to further alter portions of the carbon-containing material previously beneath the UV-opaque mask.

Some example alternative implementations are summarized below in Table 2:

TABLE 2

| Manufacturing Process Aspect(s) | Result(s) |
| --- | --- |
| Add a hardener or binder to the carbon-containing materials | UV treatment causes curing and hardening to a controllable degree (such as to be more rigids or more flexible) |
| Use the UV photon to ablate some of the carbon-containing material | Form patterns in the carbon-containing material that absorb an analyte into the carbon-containing material and/or that increase coupling between the carbon-containing material and the electrode. |
| Deposit a slurry of carbon-containing materials over a sheet of conductive, semi-conductive, or non-conductive material. | Low cost, high-volume manufacture of analyte-sensing devices. |
| Add metallic and/or semiconducting and/or dielectric, and/or polymeric materials to the carbon-containing materials (such as to the slurry) to form an open-pore matrix. | Facilitates permeation of certain analytes into the matrix and/or tunes the matrix to be sensitive to particular analytes. |
| Add metallic and/or semiconducting and/or dielectric, and/or polymeric materials to the carbon-containing materials (such as to the slurry) to form an open-pore matrix. | Tunes the matrix to be sensitive to particular analytes and/or facilitates permeation of certain analytes into the matrix. |
| Maintain low temperatures during processing. | Avoid loss of conductivity that may occur at higher temperatures (such as when polymers unwantedly coat metallics). |

Figure 9:
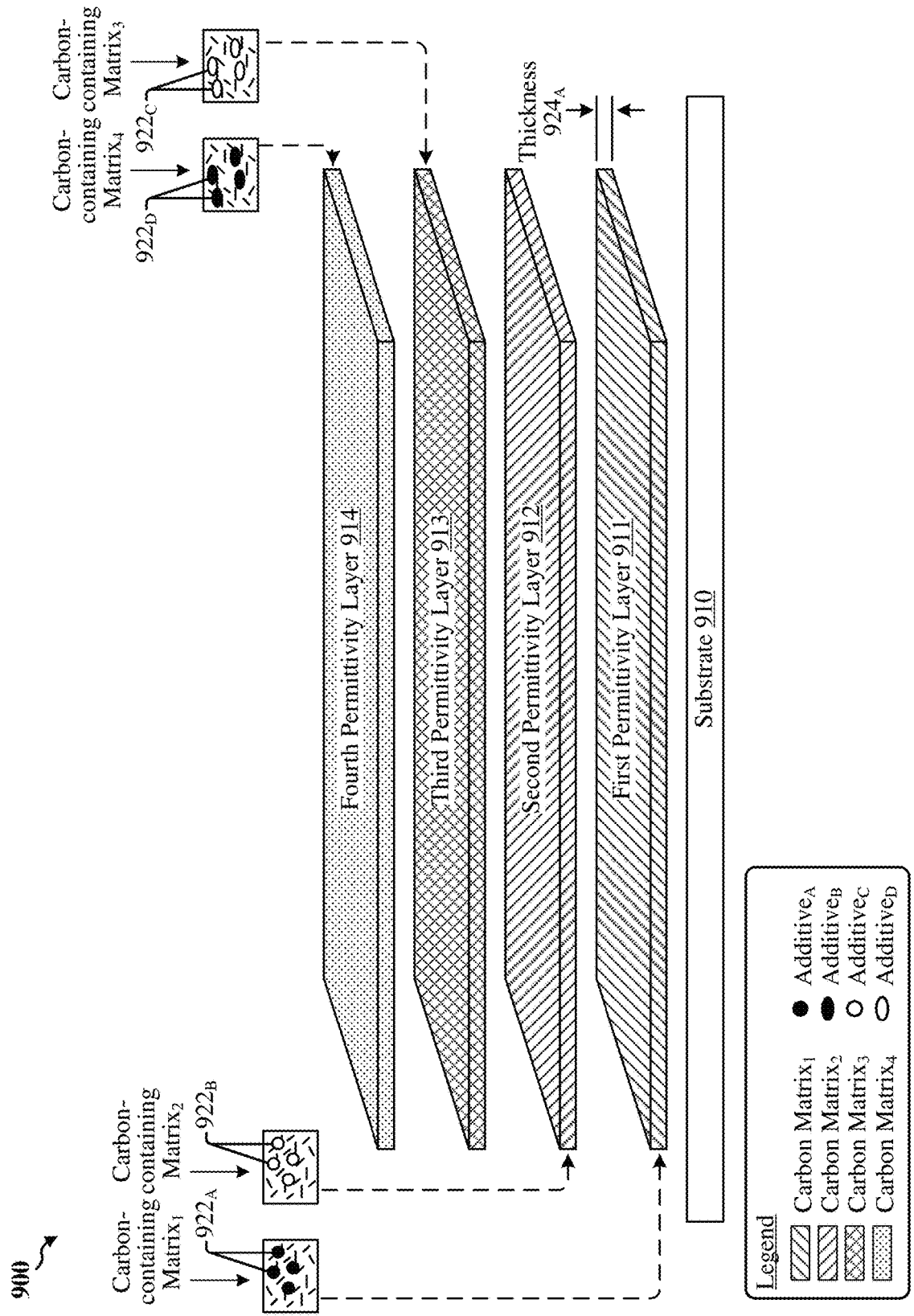
FIG. 9 shows another sensor array, according to some implementations.

FIG. 9 shows another sensor array 900, according to some implementations. The sensor array 900 includes a plurality of layers 911-914 of individually-functionalized carbon-containing materials. As shown, the layers 911-914 are successively disposed to form a stack of layers, with the first layer 911 disposed on the substrate 910. Each layer is formed of a corresponding individually-functionalized carbon-containing matrix (such as carbon matrix1, carbon matrix2, carbon matrix3, carbon matrix4), wherein each individually-functionalized carbon-containing matrix includes a respective additive A-D). The combinations of carbon-containing matrices and additive may be selected based on the particular combination's sensitivity to a particular analyte of interest.

In forming the analyte sensor array, the different layers can be deposited using any known technique. Furthermore, each of the different layers can be configured to be of a particular thickness. Strictly as one example, and as shown, a first deposited layer can have a first thickness 924 in a first range (such as 10 nm-100 nm, whereas another deposited layer can have a thickness in a different range (such as 500 nm-1,000 nm), and so on. The particular thickness of a particular layer can be selected based upon any combination of:

characteristics of the additive for that particular layer, and/or characteristics of the analyte of interest, and/or innate binary-tertiary interactions by and between the constituents of the layer.

In some implementations, the open pore structure of carbon-based sensing materials disclosed herein may allow certain analytes to more easily penetrate the materials and/or to more easily interact with carbon matrices within the materials. As such, these open pores may increase the sensitivity of sensors disclosed herein to analytes than conventional analyte detection systems.

FIG. 10A shows an example sensor configuration 1000A, according to some implementations. The sensor configuration 1000A includes mappings between sensors of an analyte detection system and various analytes, according to some implementations. For example, the 3D graphene-based sensing materials of the carbon-based sensors 120 of FIG. 1 may be or include the carbon recipes shown in the sensor configuration 1000A. That is, in a configuration in which the sensor array 120 includes 8 carbon-based sensors 120, each sensor may have a corresponding carbon recipe as shown by the example sensor configuration 1000A. For example, a first sensor may be cobalt oxide ($Co_2O_3$) decorated CNO and produce a percentage change in current (% $\Delta I$) over initial current ($I_0$) and/or percentage increase in measured impedance of 9.26244%, and so on. In this way, the carbon recipes of the sensor configuration 1000A may be used to configure the carbon-based sensors to detect and identify different analytes (such as TATP, DNT, $H_2S$, and so on), even at relatively low concentration levels, based on their respective chemical fingerprints. As such, the sensing devices disclosed herein may be able to detect relatively low concentrations of analytes and/or other chemical threat agents, even in the presence of common interferents.

FIG. 10B shows another example sensor configuration 1000B, according to some implementations. The sensor configuration 1000B may be similar to the sensor configuration 1000A of FIG. 10A, for example, such that:

Sensor No. 1: Carbon #29, corresponding to carbon nano-onion (CNO) oxides produced in a thermal reactor; cobalt(II) acetate ($C_4H_6CoO_4$), the cobalt salt of acetic acid (often found as tetrahydrate $Co(CH_3CO_2)_2 \cdot 4\ H_2O$, abbreviated $Co(OAc)_2 \cdot 4H_2O$, is flowed into the thermal reactor at a ratio of approximately 59.60 wt % corresponding to 40.40 wt % carbon (referring to carbon in CNO form), resulting in the functionalization of active sites on the CNO oxides with cobalt, showing cobalt-decorated CNOs at 15,000× and 100,000× levels, respectively; suitable gas mixtures used to produce Carbon #29 and/or the cobalt-decorated CNOs may include the following steps:

Ar purge 0.75 standard cubic feet per minute (scfm) for 30 min;

Ar purge changed to 0.25 scfm for run;

temperature increase: 25° C. to 300° C. 20 mins; and temperature increase: 300°-500° C. 15 mins.

Figure 11A:
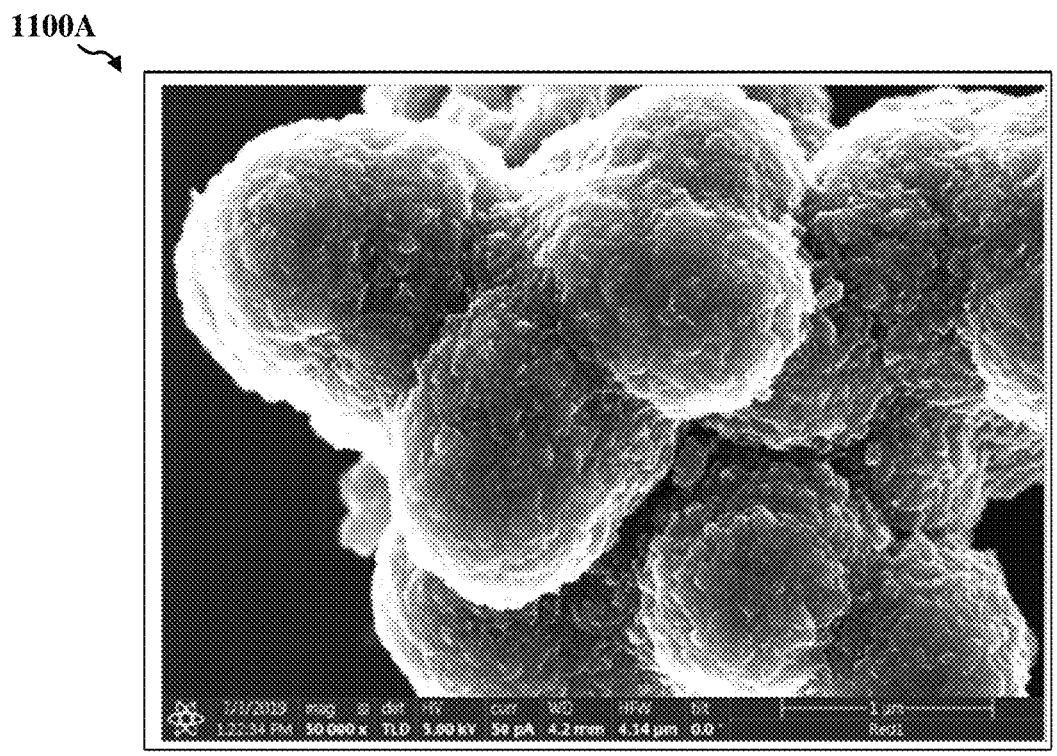
FIGS. 11A-11G show illustrations of various structured carbon materials that can be used in the sensing devices disclosed herein, according to some implementations.

Sensor No. 2: corresponding to TG JM (thermal graphene jet milled; thermal reactor carbon unfunctionalized) as shown in FIG. 11A.

Figure 11B:
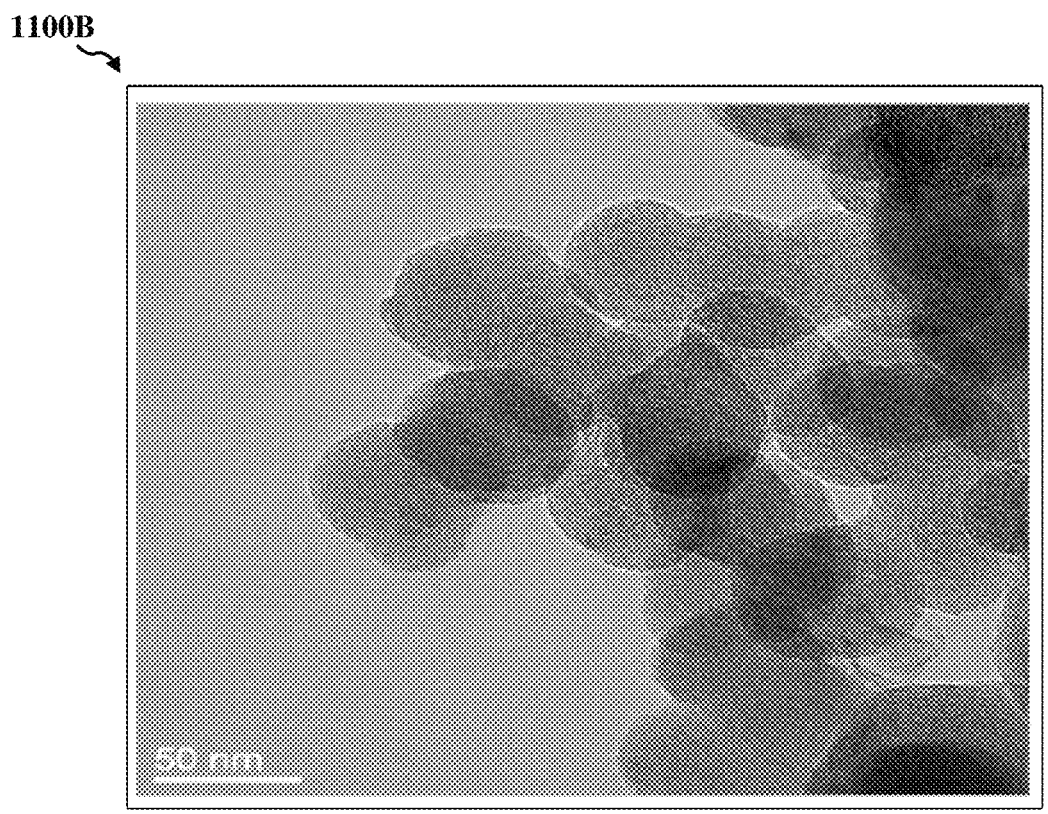

Sensor No. 3: Carbon #19, corresponding to "DXR" (as characterized by FIGS. 5A and/or 5B) type or configuration carbons produced in a microwave reactor (such as a reactor coupled to a microwave source such that microwave energy propagates through the reactor exciting carbon-containing gases and/or plasmas inside the reactor); silver acetate ($CH_3CO_2Ag$), a white, crystalline solid particulate substance suspended in carrier gas to create silver acetate vapor, is flowed into the microwave reactor at a ratio of approximately 58.18 wt % corresponding to 41.82 wt % carbon (referring to carbon in DXR form), resulting in the functionalization of active sites on the DXR configuration carbons with silver as substantially shown in FIG. 11D (in undecorated form) and/or in FIG. 11G (showing actual decoration with cobalt instead of silver). Example gas mixtures used to produce Carbon #19 and/or the silver-decorated DXR carbons substantially shown in FIGS. 11D and 11G may include the following steps:

flow of carrier gas over DXR carbon structures at a volume ratio of 6.7% $H_2$ per 93.3% Ar for approximately 1 minute and 8 seconds Sensor No. 4: CNO (carbon nano-onion; thermal reactor carbon unfunctionalized) as shown in FIG. 11B.

Sensor No. 5: Carbon #16, corresponding to "DXR" (as characterized by FIGS. 5A and/or 5B) type or configuration carbons produced in a microwave reactor; iron(II) acetate, a white solid particulate substance suspended in carrier gas to create iron acetate vapor, is flowed into the microwave reactor at a ratio of approximately 65.17 wt % corresponding to 34.83 wt % carbon (referring to carbon in DXR form), resulting in the functionalization of active sites on the DXR configuration carbons with silver as substantially shown in FIG. 11D (in undecorated form) and/or in FIG. 11G (showing actual decoration with cobalt instead of iron). Example gas mixtures used to produce Carbon #16 and/or the iron-decorated DXR carbons substantially shown in FIGS. 11D and 11G may include the following steps:

flow of carrier gas over DXR carbon structures at a volume ratio of 6.7% $H_2$ per 93.3% Ar for approximately 1 minute and 13 seconds.

Sensor No. 6: Carbon #1, corresponding to "Anvel" (as characterized by FIG. 7C) type or configuration carbons produced in a microwave reactor; platinum(II) bis(acetylacetonate), a coordination compound with the formula $Pt(O_2C_5H_7)_2$, abbreviated Pt2, is flowed as a particulate dispersed in carrier gas to create platinum(II) bis(acetylacetonate) vapor, is flowed into the microwave reactor at a ratio of approximately 76.62 wt % corresponding to 23.38 wt % carbon (referring to carbon in Anvel form), resulting in the functionalization of active sites on the Anvel configuration carbons with platinum as substantially shown in FIG. 11C (in undecorated form); suitable gas mixtures used to produce Carbon #1 and/or the undecorated Anvel carbons substantially shown in FIG. 11C may include the following steps:

flow of carrier gas over Anvel carbon structures at a volume ratio of 6.7% $H_2$ per 93.3% Ar for approximately 15 minutes Sensor No. 7: Carbon #6, corresponding to "Anvel" (as characterized by FIG. 7C) type or configuration carbons produced in a microwave reactor; palladium(II) acetate, a chemical compound of palladium described by the formula $[Pd(O_2CCH_3)_2]_n$, abbreviated $[Pd(OAc)_2]_n$, is flowed as a particulate dispersed in carrier gas to create palladium(II) acetate vapor, is flowed into the microwave reactor at a ratio of approximately 65.17 wt % corresponding to 34.83 wt % carbon (referring to carbon in Anvel form), resulting in the functionalization of active sites on the Anvel configuration carbons with platinum as substantially shown in FIG. 11C (in undecorated form). Example gas mixtures used to produce Carbon #6 and/or the palladium-decorated Anvel carbons substantially shown in FIG. 11C may include the following steps:

flow of carrier gas over Anvel carbon structures at a volume ratio of 6.7% $H_2$ per 93.3% Ar for approximately 15 minutes.

Sensor No. 8: 1,3-diaminonaphthalene complexed to TG-JM, such as that shown in FIG. 11A, to produce an organically modified carbon.

Figure 11C:
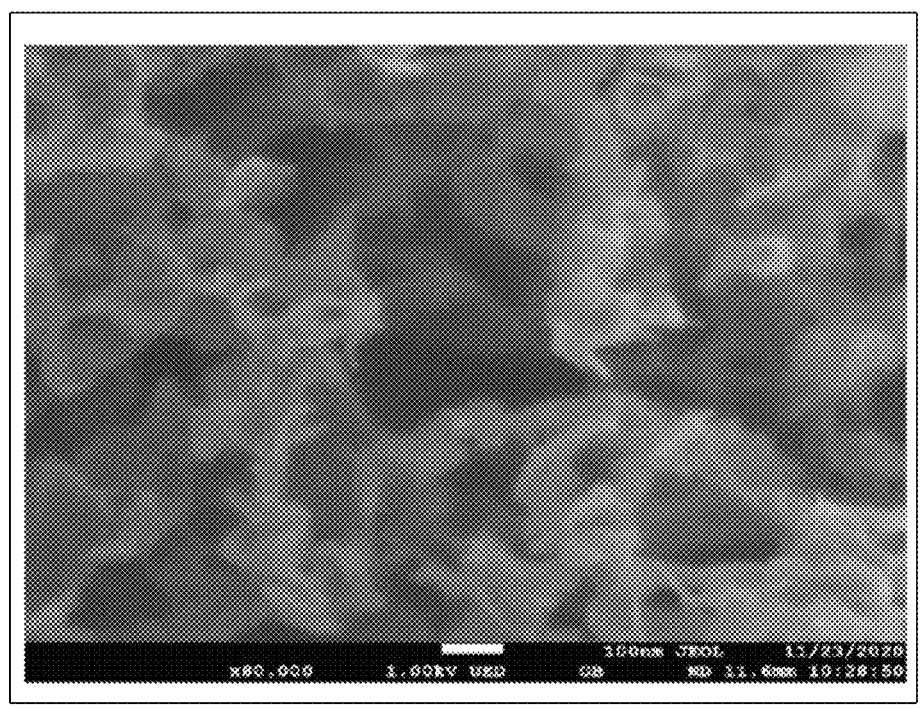
Figure 11D:
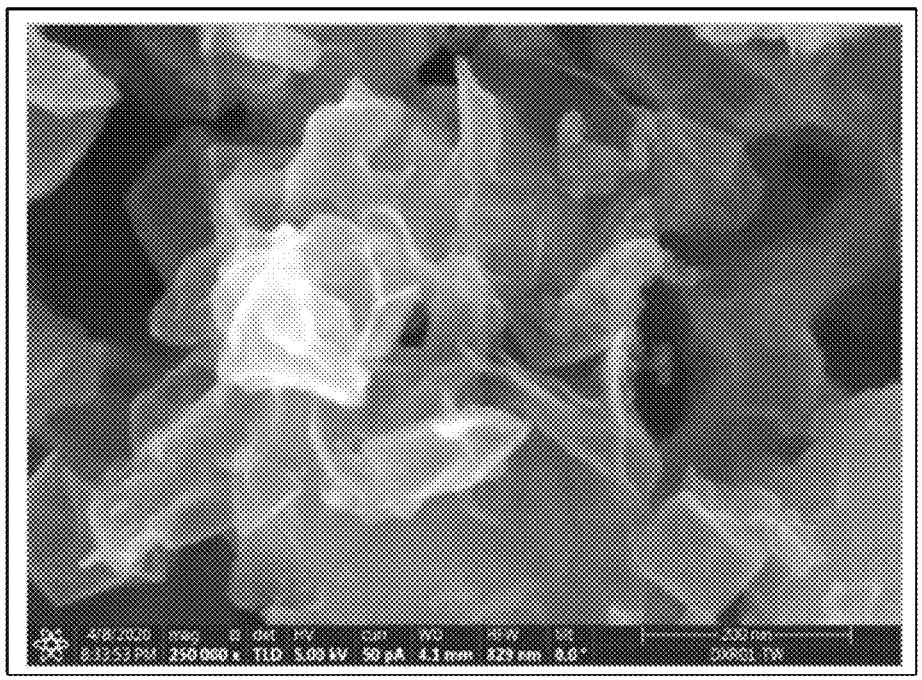
Figure 11E:
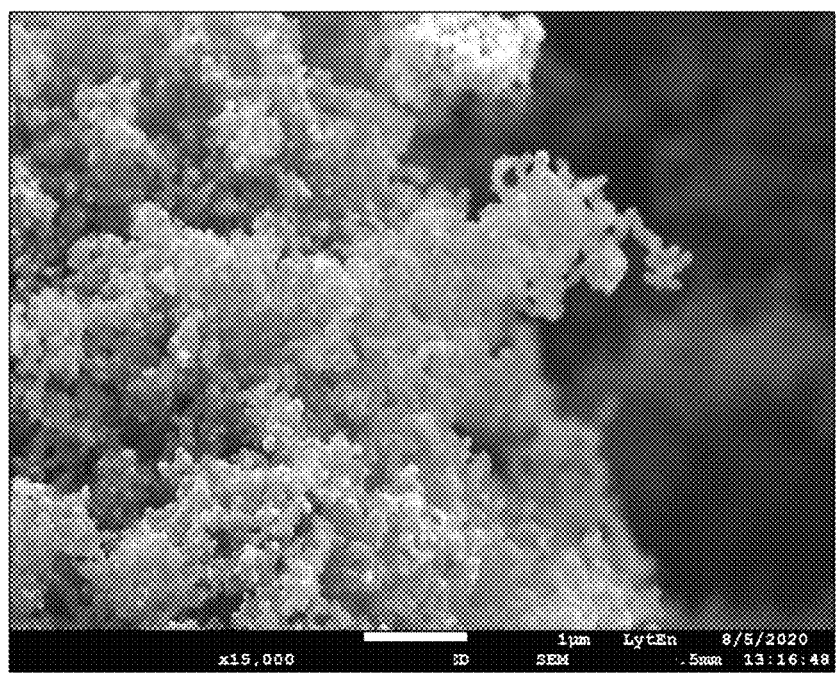
Figure 11F:
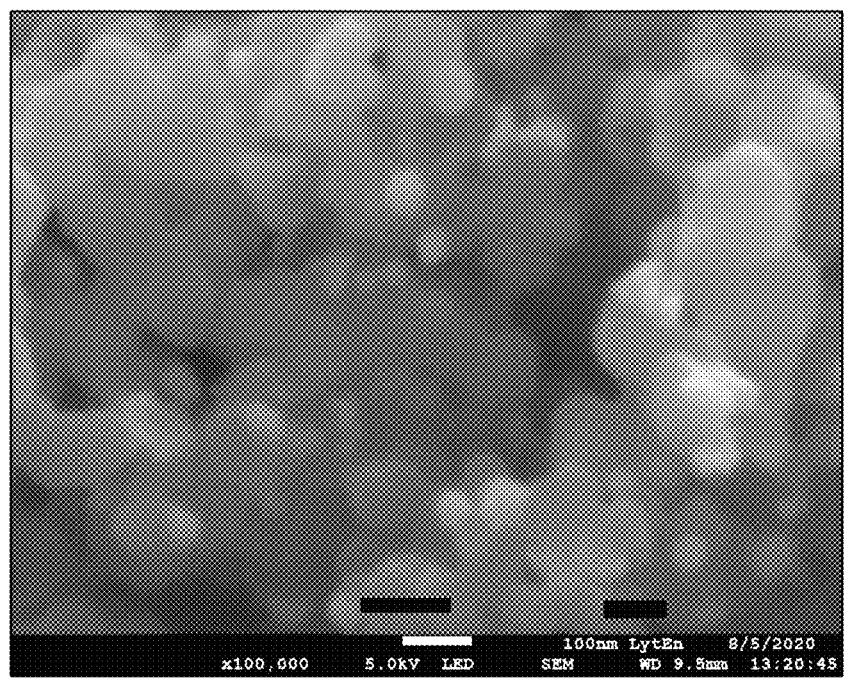
Figure 11G:
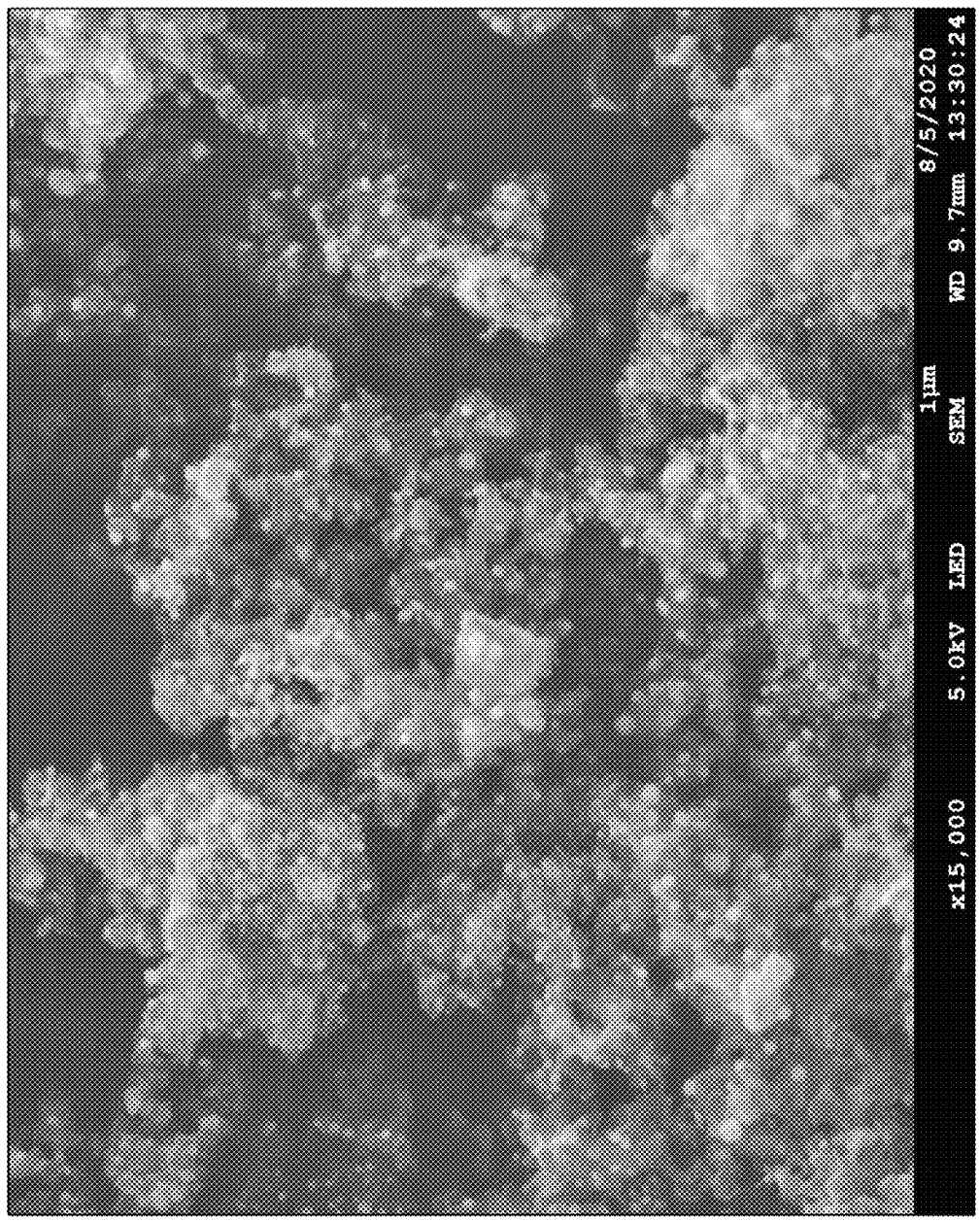

FIGS. 11A-11G show illustrations of various structured carbon materials that can be used in the sensing devices disclosed herein, according to some implementations. For example, FIG. 11A shows a micrograph 1100A of thermogravimetric (TG) carbons, according to various implementations. FIG. 11B shows a micrograph 1100B of undecorated CNOs, according to various implementations. FIG. 11C shows a micrograph 1100C of Anvel carbons, according to various implementations. FIG. 11D shows a micrograph 1100D of DXR carbons, according to various implementations. FIG. 11E shows a micrograph 1100E of cobalt decorated CNOs at a magnification level of 15,000×, according to various implementations. FIG. 11F shows a micrograph 1100F of cobalt decorated CNOs at a magnification level of 100,000×, according to various implementations. FIG. 11G shows a micrograph 1100G of a cobalt decorated DXR carbons, according to various implementations.

In contrast to a conventional 2D graphene material, the 3D graphene sensing materials disclosed by the present implementations may be designed to have a convoluted 3D structure to prevent graphene restacking, avoiding several drawbacks of using 2D graphene as a sensing material. This process also increases the areal density of the materials, yielding higher analyte adsorption sites per unit area, thereby improving chemical sensitivity, as made possible by a corresponding library of carbon allotropes used to customize the sensor arrays disclosed herein to chemically fingerprint leaked analytes for multiple applications.

The structured carbon materials shown in FIGS. 11A-11G may be produced using flow-through type microwave plasma reactors configured to create pristine 3D graphene particles continuously from a hydrocarbon gas at near atmospheric pressures. Operationally, as the hydrocarbon flows through a relatively hot zone of a plasma reactor, free carbon radicals may be formed that flow further down the length of the reactor into the growth zone where 3D carbon particulates (based on multiple 2D graphenes joined together) are formed and collected as fine powders. The density and composition of the free-radical carbon-inclusive gaseous species may be tuned by gas chemistry and microwave (MW) power levels. By controlling the reactor process parameters, these reactors may produce carbons with a wide, yet tunable, range of morphologies, crystalline order, and sizes (and distributions). For example, possible sizes and distributions may range from flakes (few 100 nm to μm wide and few nm thin) to spherical particles (10 s of nm in diameter) to graphene clusters (10 s of μm). The 3D nature of the materials prevents agglomeration effectively allowing for the materials to be disseminated as un-agglomerated particles. As a result, highly responsive and selective sensing materials can be produced. Graphene, an atomically thin two dimensional (2D) material, has many advantageous properties for sensing, including outstanding chemical and mechanical strength, high carrier mobility, high electrical conductivity, high surface area, and gate-tunable carrier density.

To improve the chemical selectivity, the 3D graphenes of the presently disclosed graphenes may be functionalized with various reactive materials in such a manner that the binding of target molecules and the carbon may be optimized. This functionalization step along with the ability to measure the complex impedance of the exposed sensor may be critical for efficient and selective detection of analytes. For example, different metal nanoparticles or metal oxide nanoparticles may be decorated on the surface of 3D graphenes to selectively detect hydrogen peroxide (a TATP degradation product) as peroxides are known to react with different metals. Further, nanoparticle decorated graphene structures may act synergistically to offer desirable and advantageous properties for sensing applications.

Figure 12A:
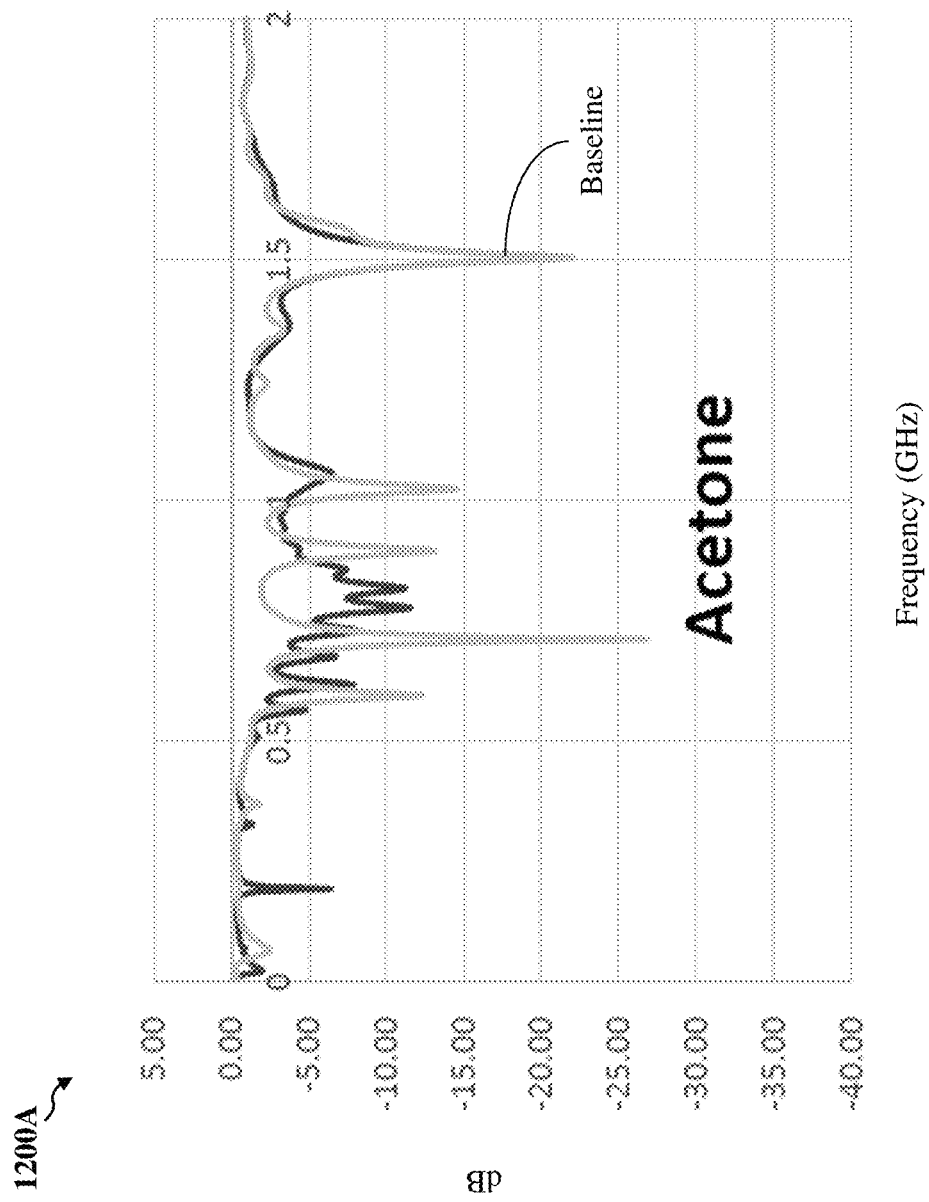
FIGS. 12A-12F show example frequency responses of resonance impedance sensors to various analytes, according to some implementations.
Figure 12B:
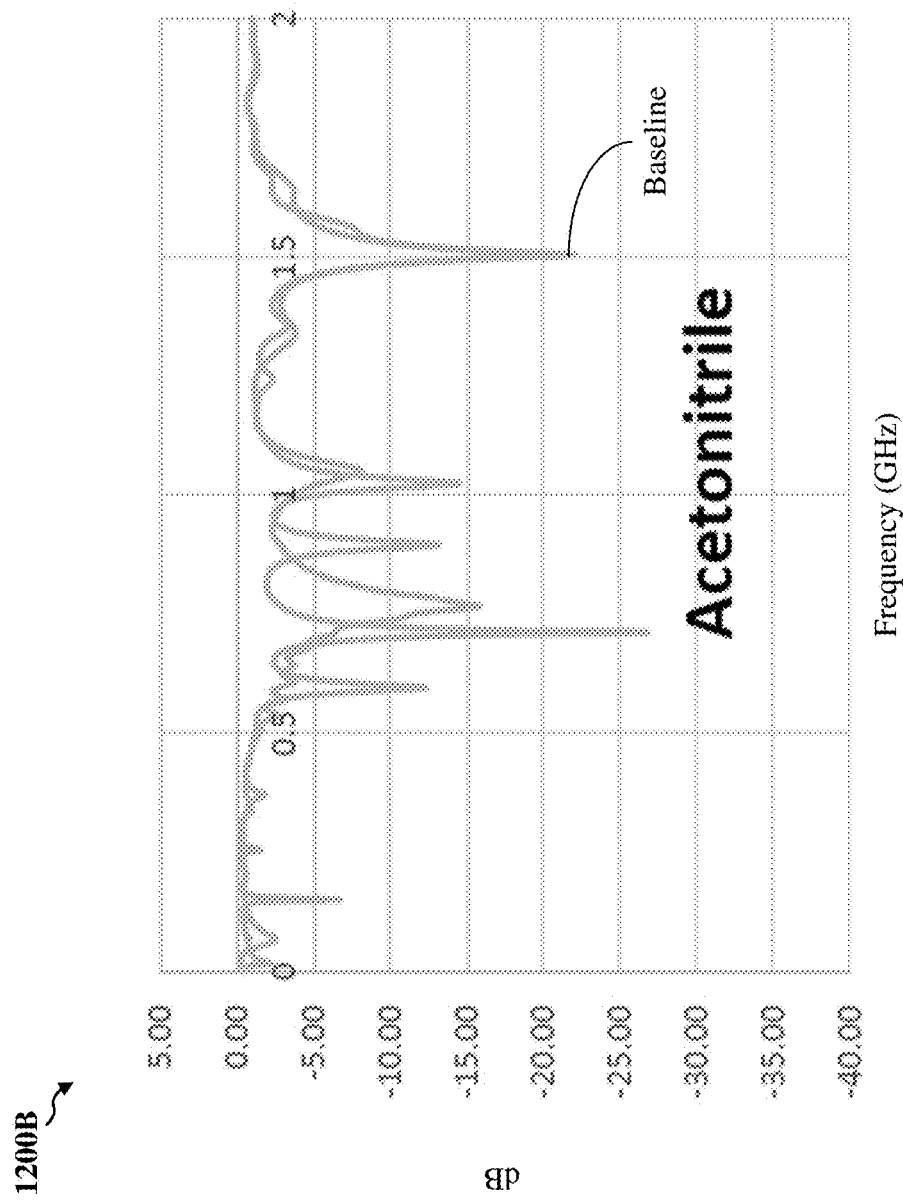
Figure 12C:
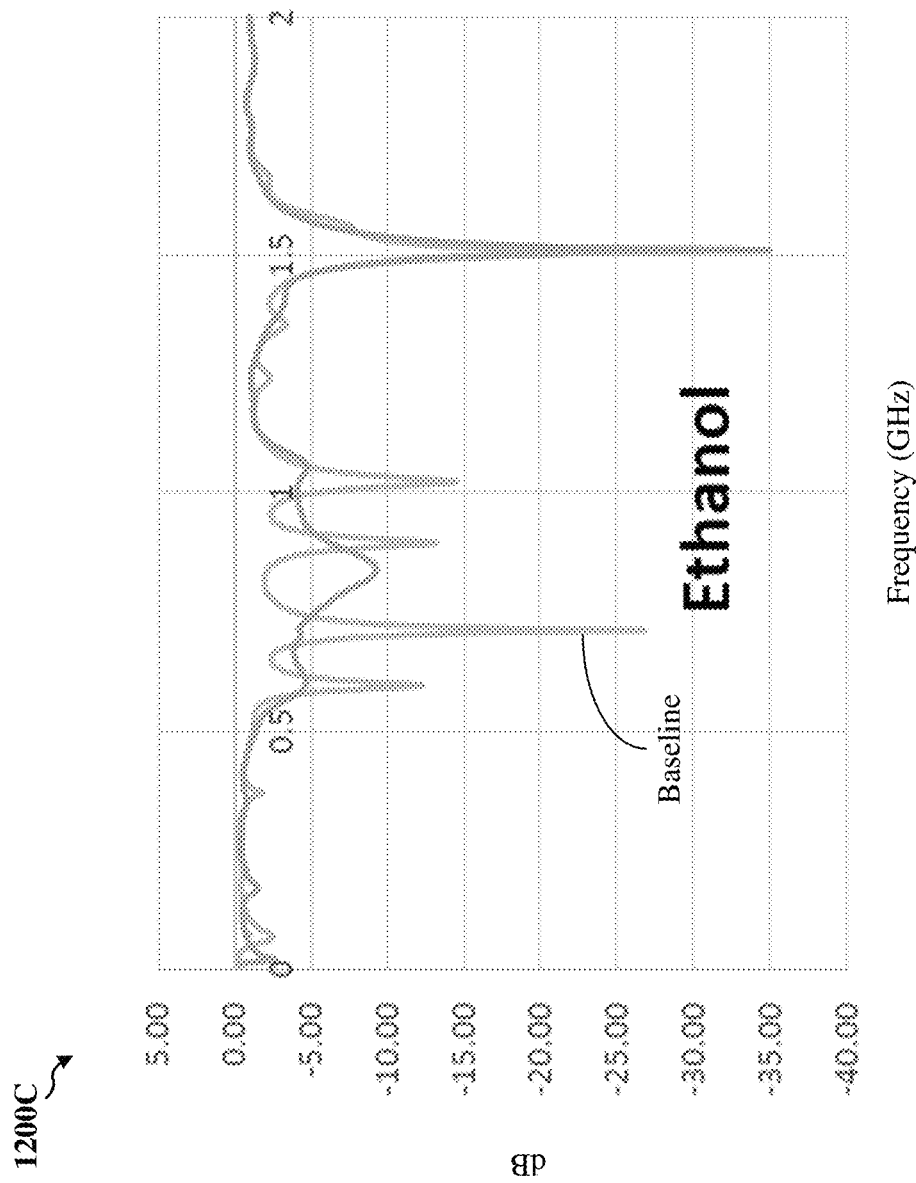
Figure 12D:
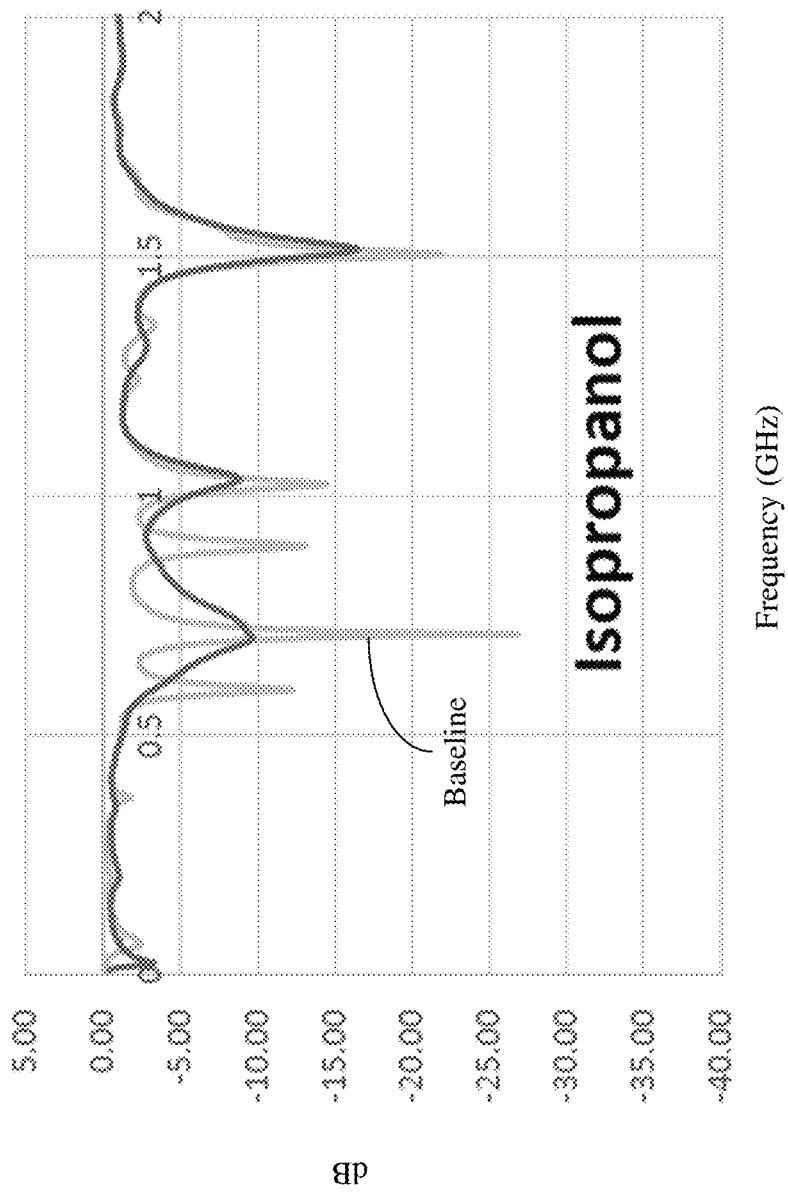
Figure 12E:
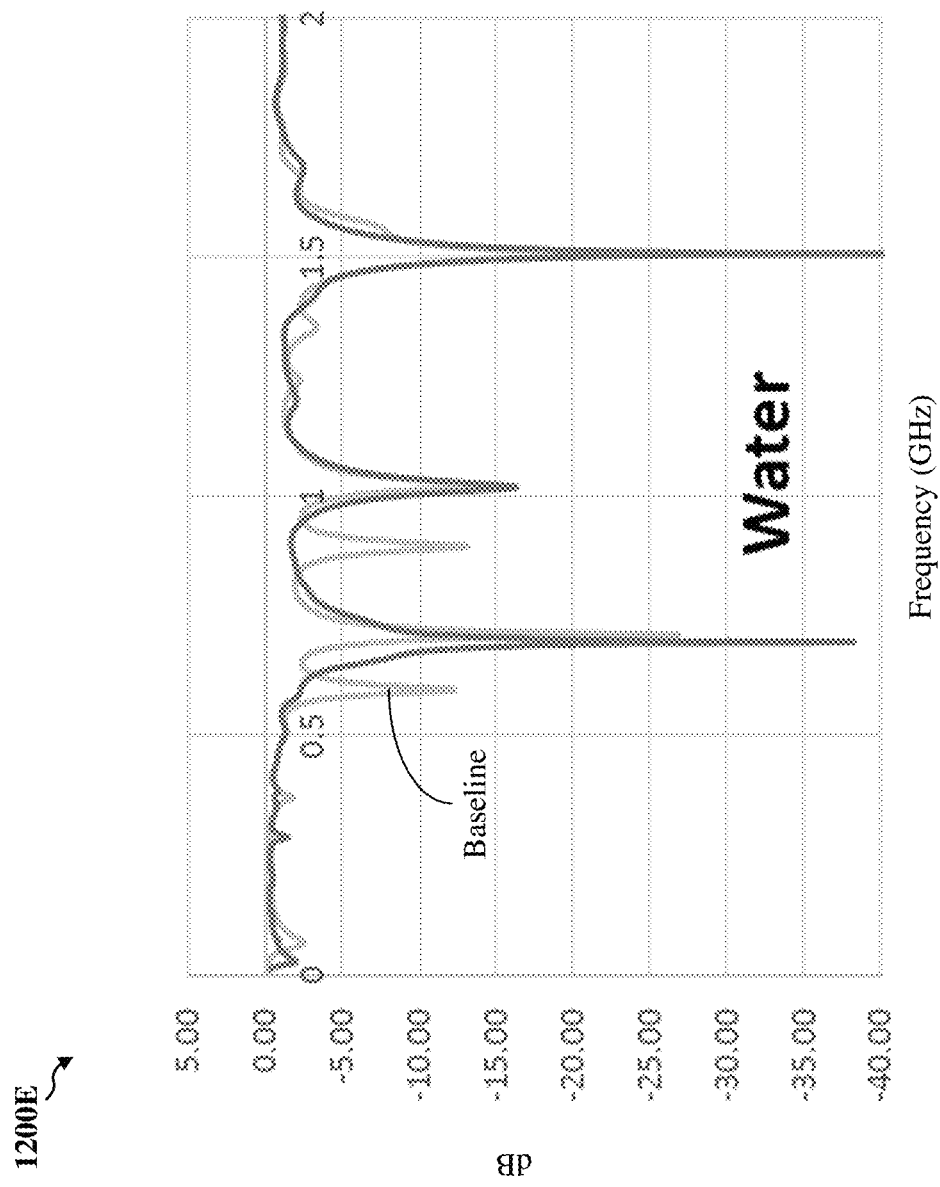
Figure 12F:
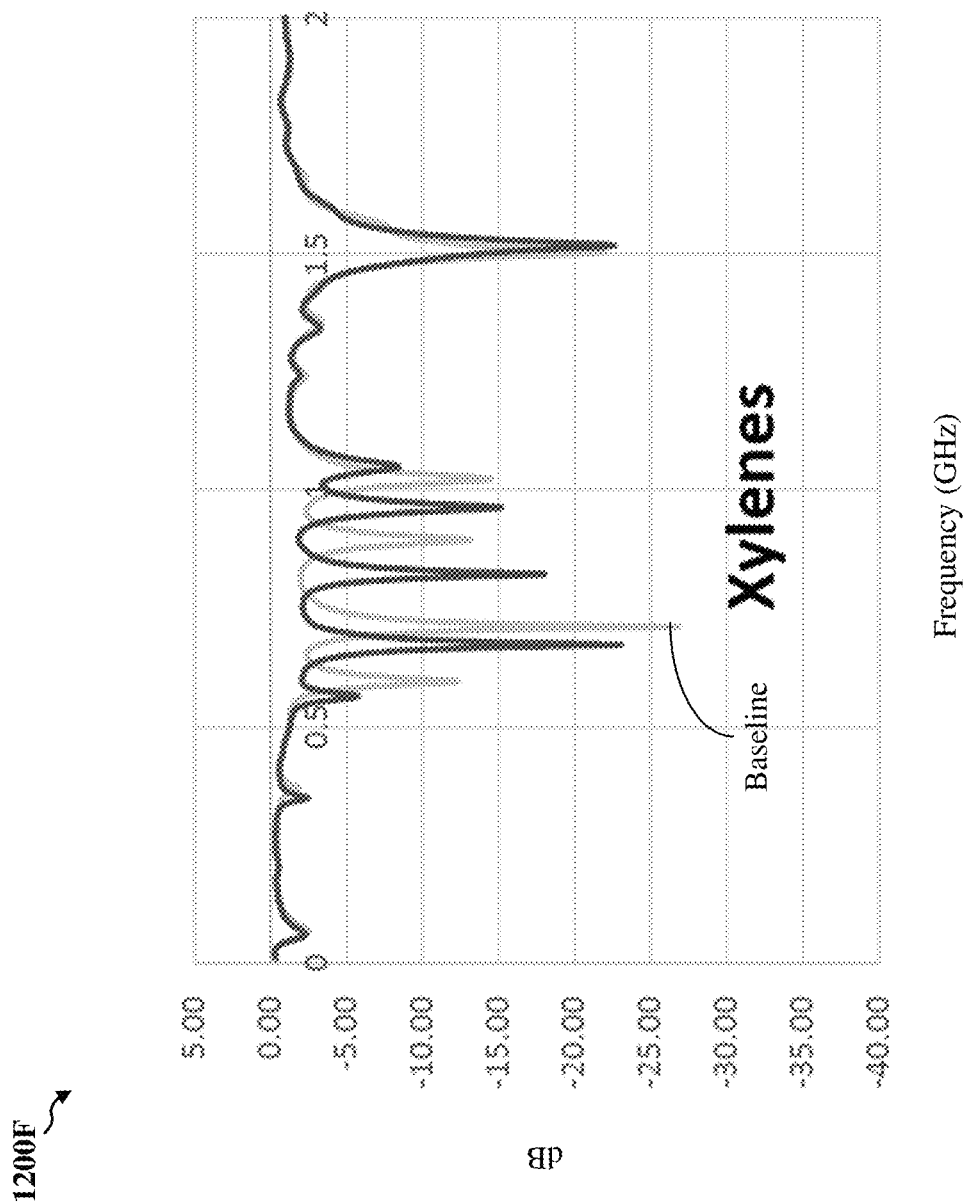

FIGS. 12A-12F show example frequency responses of resonance impedance sensors to various analytes, according to some implementations. Specifically, FIG. 12A shows an example frequency response 1200A of sensors 120 to alongside a baseline or reference frequency response. Specifically, FIG. 12A shows an example frequency response 1200A of sensors 120 to acetone alongside a baseline or reference frequency response. FIG. 12B shows an example frequency response 1200B of sensors 120 to acetonitrile alongside a baseline or reference frequency response. FIG. 12C shows an example frequency response 1200C of sensors 120 to Ethanol alongside a baseline or reference frequency response. FIG. 12D shows an example frequency response 1200A of sensors 120 to isopropanol alongside a baseline or reference frequency response. FIG. 12E shows an example frequency response 1200E of sensors 120 to water alongside a baseline or reference frequency response. FIG. 12F shows an example frequency response 1200F of sensors 120 to xylenes alongside a baseline or reference frequency response.

Figure 13A:
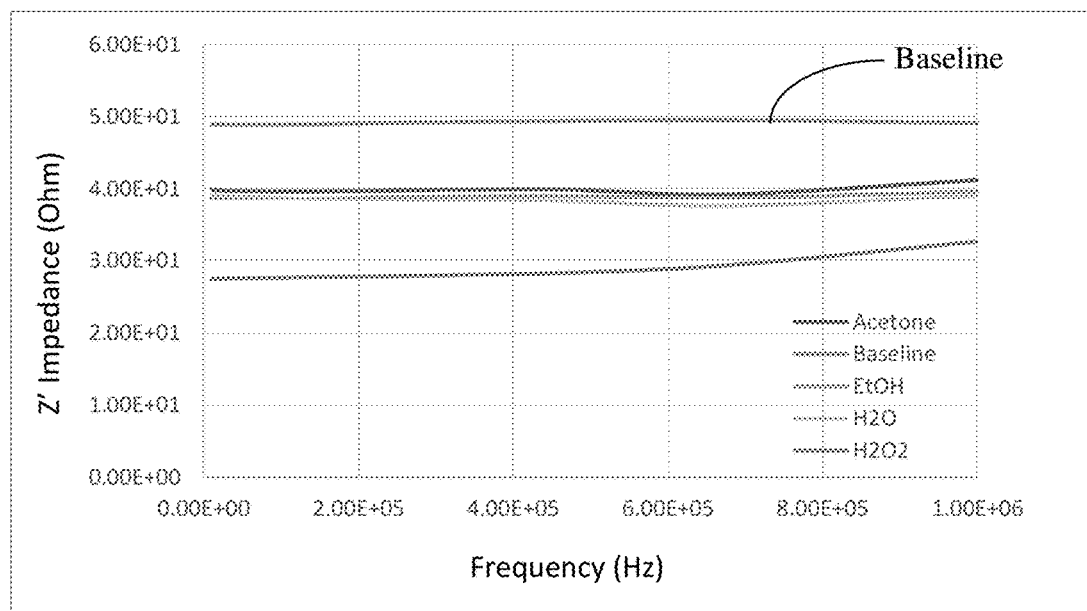
FIG. 13A shows the real (Z') impedance component of an example frequency response of electrochemical impedance sensors, according to some implementations.
Figure 13B:
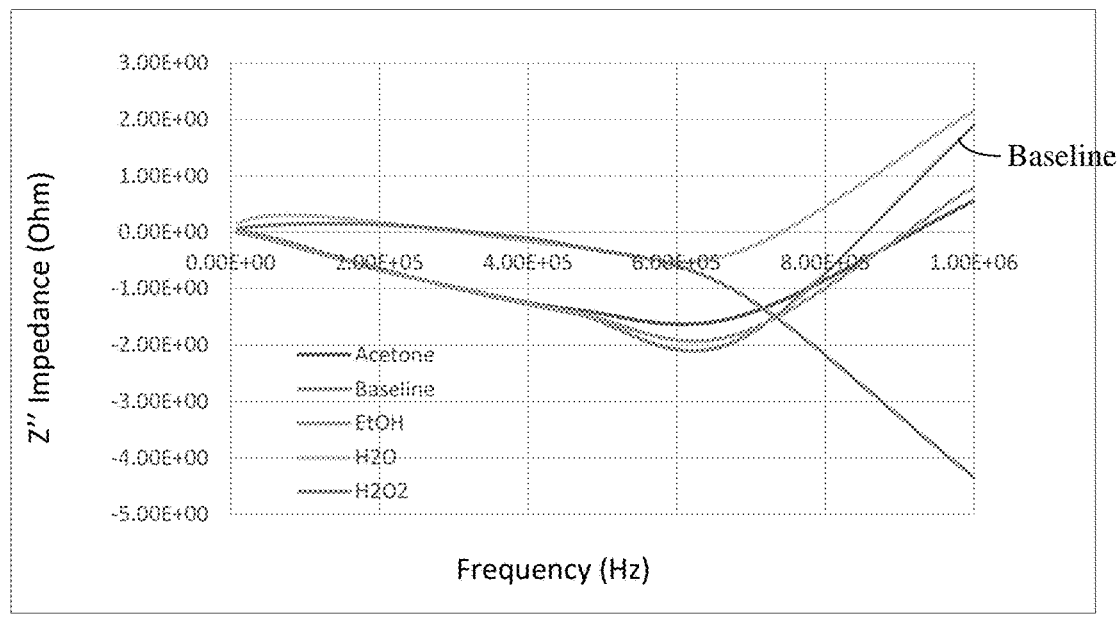
FIG. 13B shows the imaginary (Z") impedance component of an example frequency response of electrochemical impedance sensors, according to some implementations.

FIG. 13A is a graph 1300A depicting the real (Z') impedance component of example frequency responses of sensors 120 to Acetone, Ethanol (EtOH), water, and hydrogen peroxide ($H_2O_2$) alongside a baseline or reference frequency response, according to some implementations. FIG. 13B is a graph 1300B depicting the imaginary (Z") impedance component of example frequency responses of sensors 120 to Acetone, Ethanol (EtOH), water, and hydrogen peroxide ($H_2O_2$) alongside a baseline or reference frequency response, according to some implementations.

Figure 14A:
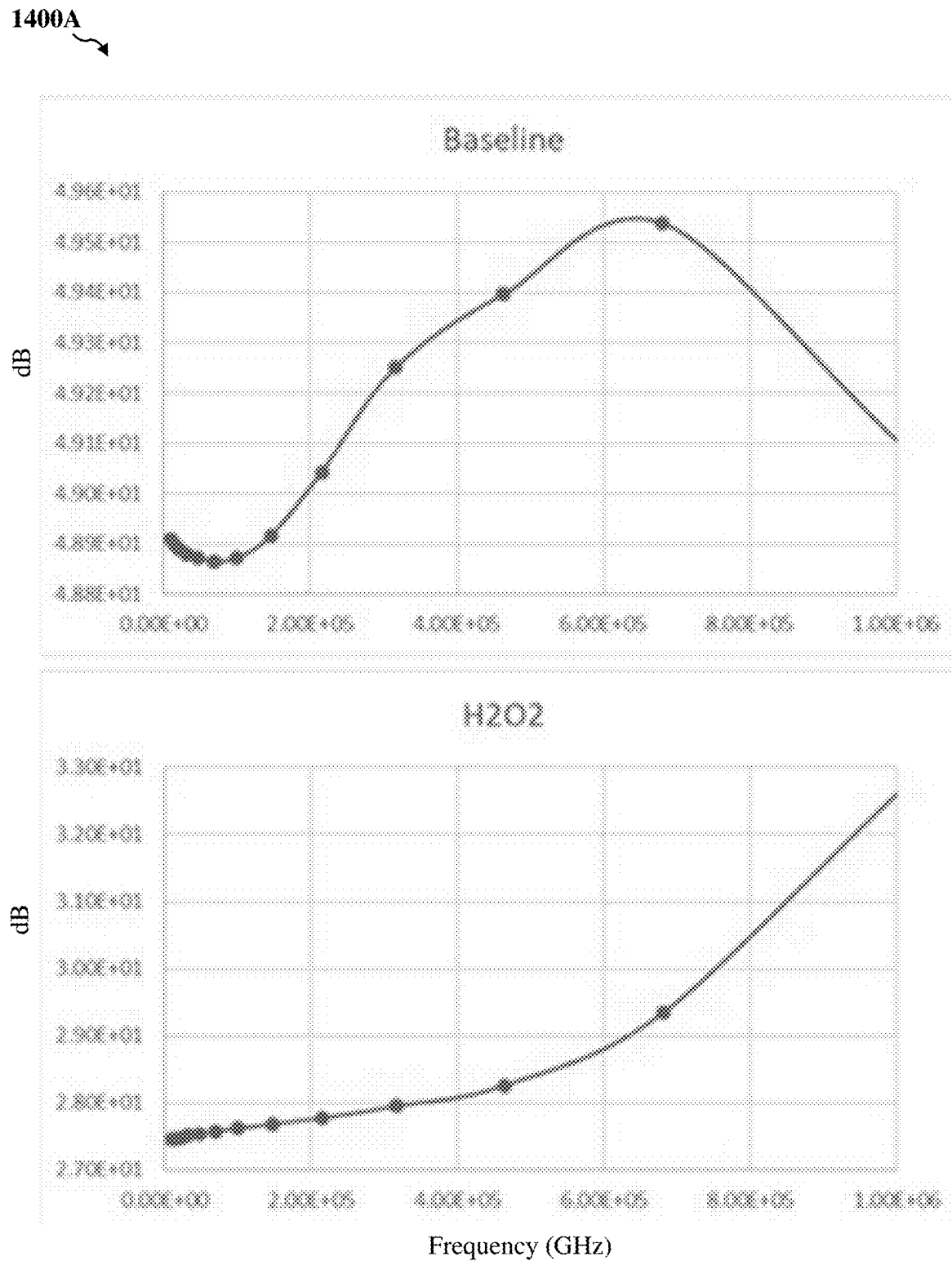
FIG. 14A shows an example baseline frequency response and an example frequency response to hydrogen peroxide, according to some implementations.
Figure 14B:
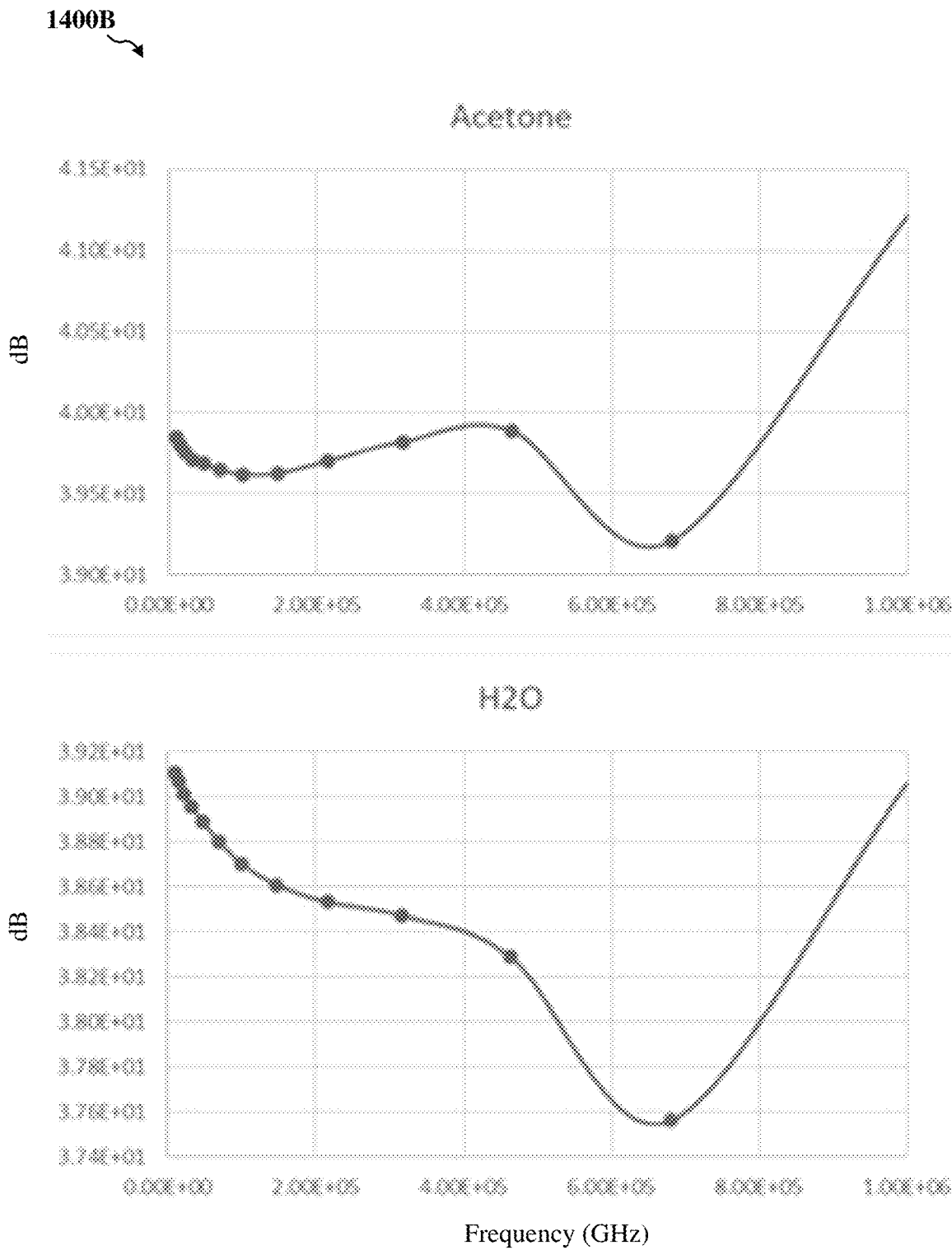
FIG. 14B shows example frequency responses to acetone and water, according to some implementations.
Figure 14C:
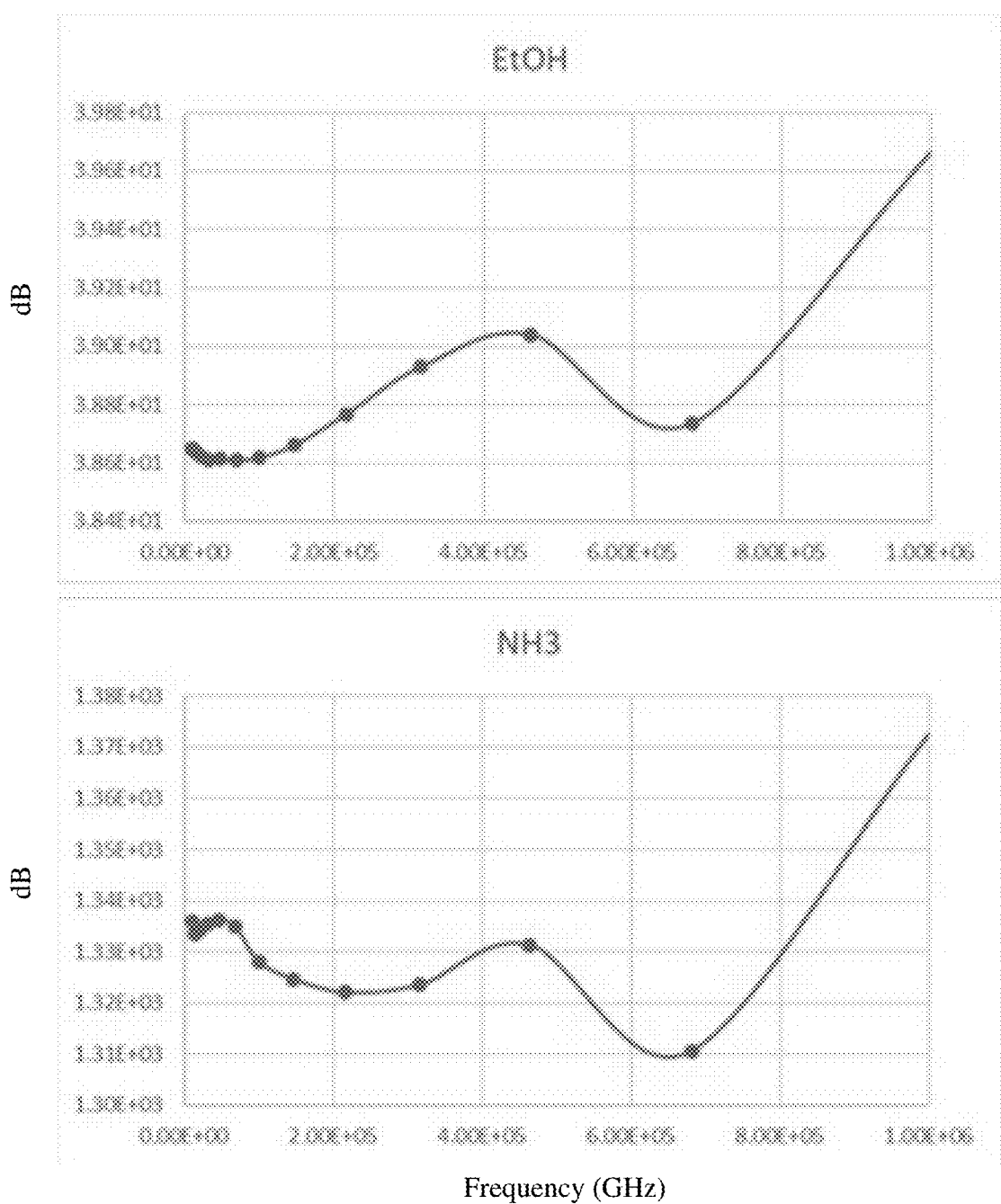
FIG. 14C shows example frequency responses to ethanol and ammonia, according to some implementations.

FIG. 14A shows an example frequency response of sensors 120 to hydrogen peroxide alongside a baseline or reference frequency response, according to some implementations. FIG. 14B shows example frequency responses of sensors 120 to acetone and water, according to some implementations. FIG. 14C shows example frequency responses to ethanol and ammonia, according to some implementations.

As used herein, a phrase referring to "at least one of" or "one or more of" a list of items refers to any combination of those items, including single members. For example, "at least one of: a, b, or c" is intended to cover the possibilities of: a only, b only, c only, a combination of a and b, a combination of a and c, a combination of b and c, and a combination of a and b and c.

The various illustrative components, logic, logical blocks, modules, circuits, operations, and algorithm processes described in connection with the implementations disclosed herein may be implemented as electronic hardware, firmware, software, or combinations of hardware, firmware, or software, including the structures disclosed in this specification and the structural equivalents thereof. The interchangeability of hardware, firmware and software has been described generally, in terms of functionality, and illustrated in the various illustrative components, blocks, modules, circuits and processes described above. Whether such functionality is implemented in hardware, firmware or software depends upon the application and design constraints imposed on the overall system.

Various modifications to the implementations described in this disclosure may be readily apparent to persons having ordinary skill in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein.

Additionally, various features that are described in this specification in the context of separate implementations also can be implemented in combination in a single implementation. Conversely, various features that are described in the context of a single implementation also can be implemented in multiple implementations separately or in any suitable subcombination. As such, although features may be described above in combination with one another, and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Further, the drawings may schematically depict one more example processes in the form of a flowchart or flow diagram. However, other operations that are not depicted can be incorporated in the example processes that are schematically illustrated. For example, one or more additional operations can be performed before, after, simultaneously, or between any of the illustrated operations. In some circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

What is claimed is:

1. A sensing device configured to monitor a battery pack, the sensing device comprising:
 a plurality of carbon-based sensors enclosed within the battery pack, each carbon-based sensor coupled between a corresponding pair of electrodes and including a plurality of 3D graphene-based sensing materials, wherein:
 the 3D graphene-based sensing materials of a first carbon-based sensor are functionalized with a first material configured to detect a presence of each analyte of a first group of analytes; and the 3D graphene-based sensing materials of a second carbon-based sensor are functionalized with a second material configured to detect a presence of each analyte of a second group of analytes, wherein the second group of analytes is a subset of the first group of analytes.

2. The sensing device of claim 1, wherein the second group of analytes is a different than the first group of analytes.

3. The sensing device of claim 1, wherein the first group of analytes includes at least twice as many different analytes as the second group of analytes.

4. The sensing device of claim 1, wherein the carbon-based sensors are stacked on one another.

5. The sensing device of claim 1, wherein the carbon-based sensors are disposed next to one another.

6. The sensing device of claim 1, wherein the carbon-based sensors comprise carbon-based inks printed on the substrate.

7. The sensing device of claim 6, wherein the first carbon-based sensor comprises a first carbon-based ink, and the second carbon-based sensor comprises a second carbon-based ink different than the first carbon-based ink.

8. The sensing device of claim 1, wherein:
the first carbon-based sensor is configured to generate a first output signal in response to detecting the presence of the one or more analytes of the first group of analytes; and
the second carbon-based sensor is configured to generate a second output signal in response to confirming the presence of the one or more analytes detected by the first carbon-based sensor.

9. The sensing device of claim 8, further comprising an input terminal to receive an alternating current.

10. The sensing device of claim 9, wherein the first and second output signals comprise currents based at least in part on the alternating current.

11. The sensing device of claim 9, wherein a first difference between the alternating current and the first output signal is indicative of the presence or absence of one or more analytes of the first group of analytes, and a second difference between the alternating current and the second output signal is indicative of the presence or absence of one or more analytes of the second group of analytes.

12. The sensing device of claim 9, wherein the first output signal indicates a change in impedance of the first carbon-based sensor caused by exposure to one or more analytes of the first group of analytes, and the second output signal indicates a change in impedance of the second carbon-based sensor caused by exposure to one or more analytes of the second group of analytes.

13. The sensing device of claim 12, wherein a relatively small impedance change of a respective carbon-based sensor indicates an absence of a corresponding group of analytes, and a relatively large impedance change of the respective carbon-based sensor indicates a presence of the corresponding group of analytes.

14. The sensing device of claim 8, further comprising an antenna configured to receive an electromagnetic signal from an external device.

15. The sensing device of claim 14, wherein the first and second output signals comprise frequency responses of the 3D graphene-based sensing materials of the first and second carbon-based sensors, respectively, to the electromagnetic signal.

16. The sensing device of claim 15, wherein:
the frequency response of the 3D graphene-based sensing materials of the first carbon-based sensor is indicative of the presence or absence of one or more analytes of the first group of analytes; and
the frequency response of the 3D graphene-based sensing materials of the second carbon-based sensor is indicative of the presence or absence of one or more analytes of the second group of analytes.

17. The sensing device of claim 16, wherein the frequency responses are based on resonant impedance spectroscopy (RIS) sensing.

18. The sensing device of claim 8, wherein at least one of the output signals indicates an operating mode of the battery pack.

19. The sensing device of claim 18, wherein:
the at least one output signal indicates a normal mode based on an absence of the analytes of the first group of analytes;
the at least one output signal indicates a maintenance mode based on the presence of one or more analytes of the first group of analytes not exceeding a threshold level; and
the at least one output signal indicates an emergency mode based on the presence of one or more analytes of the first group of analytes exceeding a threshold level.

20. The sensing device of claim 8, wherein the first output signal is indicative of a concentration level of one or more analytes of the first group of analytes, and the second output signal is indicative of a concentration level of one or more analytes of the second group of analytes.

21. The sensing device of claim 1, wherein the analytes of the first and second groups of analytes includes one or more volatile organic compounds (VOCs).

22. The sensing device of claim 21, wherein the one or more volatile organic compounds (VOCs) include any one or more of carbon dioxide ($CO_2$), carbon monoxide (CO), nitrogen dioxide ($NO_2$), one or more hydrocarbons including methane ($CH_4$), ethylene ($C_2H_4$), ethane ($C_2H_6$), or propane ($C_3H_8$), one or more acids including hydrochloric acid (HCl) or hydrofluoric acid (HF), one or more fluorinated hydrocarbons including phosphorus oxyfluoride, hydrogen cyanide (HCN), one or more aromatics including benzene ($C_6H_6$), toluene ($C_7H_8$), ethanol ($C_2H_5OH$), hydrogen, carbonate based electrolytes including ethylene carbonate ($C_3H_4O_3$), dimethyl carbonate ($C_3H_6O_3$), propylene carbonate ($C_4H_3O_3$), or one or more reduced sulfur compounds including thiols having a form of R—SH.

23. The sensing device of claim 21, wherein each of the 3D graphene-based sensing materials is configured to adsorb the VOCs.

24. The sensing device of claim 1, wherein each of the carbon-based sensors comprises a plurality of different graphene allotropes.

25. The sensing device of claim 24, wherein the plurality of different graphene allotropes of a respective carbon-based sensor includes one or more microporous pathways or mesoporous pathways.

* * * * *